US009453840B2

(12) United States Patent
Takahashi et al.

(10) Patent No.: US 9,453,840 B2
(45) Date of Patent: Sep. 27, 2016

(54) MARKERS FOR DOPAMINERGIC NEURON PROGENITOR CELLS

(75) Inventors: Jun Takahashi, Kyoto (JP); Daisuke Doi, Kyoto (JP); Bumpei Samata, Kyoto (JP); Yuichi Ono, Kobe (JP)

(73) Assignees: Kyoto University, Kyoto (JP); Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/234,361

(22) PCT Filed: Jul. 27, 2012

(86) PCT No.: PCT/JP2012/069785
§ 371 (c)(1),
(2), (4) Date: Jan. 22, 2014

(87) PCT Pub. No.: WO2013/015457
PCT Pub. Date: Jan. 31, 2013

(65) Prior Publication Data
US 2014/0193836 A1 Jul. 10, 2014

Related U.S. Application Data

(60) Provisional application No. 61/512,162, filed on Jul. 27, 2011.

(51) Int. Cl.
*C12N 15/08* (2006.01)
*G01N 33/569* (2006.01)
*C12N 5/0793* (2010.01)
*C12N 5/0797* (2010.01)

(52) U.S. Cl.
CPC ....... *G01N 33/56966* (2013.01); *C12N 5/0619* (2013.01); *C12N 5/0623* (2013.01); *C12N 2501/155* (2013.01); *C12N 2501/16* (2013.01); *C12N 2501/727* (2013.01); *C12N 2502/1394* (2013.01); *C12N 2506/02* (2013.01); *C12N 2506/45* (2013.01); *C12N 2509/00* (2013.01)

(58) Field of Classification Search
CPC .................................................. C12N 5/0619
See application file for complete search history.

(56) References Cited

U.S. PATENT DOCUMENTS

| 5,690,927 | A | 11/1997 | Major et al. |
| 6,277,820 | B1 | 8/2001 | Rosenthal et al. |
| 2001/0053519 | A1 | 12/2001 | Fodor et al. |
| 2002/0155423 | A1 | 10/2002 | Okano et al. |
| 2005/0175997 | A1 | 8/2005 | Ono et al. |
| 2006/0239978 | A1 | 10/2006 | Nakagawa et al. |
| 2006/0240432 | A1 | 10/2006 | Ono et al. |
| 2006/0292669 | A1 | 12/2006 | Takeuchi et al. |
| 2007/0122882 | A1 | 5/2007 | Nakagawa et al. |
| 2007/0254281 | A1 | 11/2007 | Ono et al. |
| 2008/0199437 | A1 | 8/2008 | Sakamoto et al. |
| 2008/0280301 | A1 | 11/2008 | Ono et al. |
| 2008/0311091 | A1 | 12/2008 | Perlmann et al. |
| 2010/0028866 | A1 | 2/2010 | Ono et al. |
| 2010/0120628 | A1 | 5/2010 | Belouchi et al. |
| 2010/0203505 | A1 | 8/2010 | Ono et al. |
| 2010/0203570 | A1 | 8/2010 | Nakagawa et al. |
| 2010/0216164 | A1 | 8/2010 | Takeuchi et al. |
| 2010/0323366 | A1 | 12/2010 | Ono et al. |
| 2011/0008769 | A1 | 1/2011 | Ono et al. |
| 2011/0229889 | A1 | 9/2011 | Ono et al. |
| 2012/0021417 | A1 | 1/2012 | Ono et al. |
| 2012/0178083 | A1 | 7/2012 | Ono et al. |
| 2012/0252021 | A1 | 10/2012 | Ono et al. |

FOREIGN PATENT DOCUMENTS

| EP | 1405909 A1 | 4/2004 |
| EP | 1447413 A2 | 8/2004 |
| JP | 2002-51775 A | 2/2002 |
| WO | WO 94/23754 A1 | 10/1994 |
| WO | WO 95/12982 A1 | 5/1995 |
| WO | WO 96/14397 A1 | 5/1996 |
| WO | WO 96/14398 A1 | 5/1996 |
| WO | WO 96/14399 A1 | 5/1996 |
| WO | WO 96/28030 A1 | 9/1996 |
| WO | WO 96/28174 A1 | 9/1996 |
| WO | WO 96/39496 A1 | 12/1996 |
| WO | WO 97/02049 A1 | 1/1997 |
| WO | WO 99/43286 A2 | 9/1999 |
| WO | WO 99/56759 A1 | 11/1999 |
| WO | WO 99/64608 A1 | 12/1999 |
| WO | WO 00/06700 A1 | 2/2000 |
| WO | WO 00/09669 A1 | 2/2000 |
| WO | WO 01/57194 A2 | 8/2001 |
| WO | WO 01/83715 | 11/2001 |
| WO | WO 02/063938 | 8/2002 |

(Continued)

OTHER PUBLICATIONS

Sonntag (Stem Cells, 2007, 25:411-418).*
Takagi (2005, Jour Clin Invest, 115:102-109).*
White and Thomas, 2012, CNS and Neurological Disorders—Drug Targets, 11:340-349.*
Hedlund, 2007, Stem Cell, 25:1126-1135.*
Pruszak, 2007, Stem Cells, 25:2257-2268.*
Zeng, 2004, Stem cells, 22:925-940.*
Raye, 2007, European Journal of Neuroscience, 25:1961-1970.*
Nefzger, 2012, Stem Cells, 30:1349-1361.*
Office Action in CN App. Ser. No. 200580031914.3, dated Feb. 3, 2012, 8 pages (with English translation).
International Search Report issued for International Application No. PCT/JP05/013453 dated Oct. 25, 2005, 6 pages.
Decision of Rejection in JP App. Ser. No. 2006-355330, dated Oct. 18, 2010, 2 pages (English translation).

(Continued)

*Primary Examiner* — Valarie Bertoglio
(74) *Attorney, Agent, or Firm* — Fish & Richardson P.C.

(57) ABSTRACT

The present invention provides a method for selecting dopaminergic neuron progenitor cells, which comprises detecting any one or more of markers selected from the group consisting of CD15 (SSEA-1), CD24, CD46, CD47, CD49b, CD57, CD58, CD59, CD81, CD90, CD98, CD147, CD184, Disalogangliosid GD2, SSEA-4, CD49f, SERINC4, CCR9, PHEX, TMPRSS11E, HTR1E, SLC25A2, Ctxn3, Ccl7, Chrnb4, Chrna3, Kcnv2, Grm2, Syt2, Lim2, Mboat1, St3gal6, Slc39a12, Tacr1, Lrtm1, Dscam and CD201.

7 Claims, 3 Drawing Sheets

(56) References Cited

FOREIGN PATENT DOCUMENTS

| WO | WO 02/074906 A2 | 9/2002 |
|---|---|---|
| WO | WO 02/103007 A1 | 12/2002 |
| WO | WO 03/010329 A2 | 2/2003 |
| WO | WO 03/106657 | 12/2003 |
| WO | WO 2004/005458 A2 | 1/2004 |
| WO | WO 2004/038018 | 5/2004 |
| WO | WO 2004/048511 A2 | 6/2004 |
| WO | WO 2004/048573 | 6/2004 |
| WO | WO 2004/048938 A2 | 6/2004 |
| WO | WO 2004/065599 | 8/2004 |
| WO | WO 2004/081172 | 9/2004 |
| WO | WO 2004/094598 A2 | 11/2004 |
| WO | WO 2004/094651 A2 | 11/2004 |
| WO | WO 2005/052190 A1 | 6/2005 |
| WO | WO 2006/009241 A1 | 1/2006 |
| WO | WO 2007/021003 A1 | 2/2007 |
| WO | WO 2007/021004 A1 | 2/2007 |
| WO | WO 2007/119759 A1 | 10/2007 |

OTHER PUBLICATIONS

International Search Report issued in PCT App. Ser. No. PCT/JP04/17574, dated Feb. 22, 2005, 2 pages.
Decision of Rejection in CN App. Ser. No. 200480041020.8, dated Jul. 24, 2009, 7 pages (with English translation).
Office Action in CN App. Ser. No. 200480041020.8, dated Feb. 12, 2010, 8 pages (with English translation).
Office Communication issued for EP App. Ser. No. 04819438.5, dated Feb. 7, 2008, 6 pages.
Office Communication issued for EP Ser. Appl. No. 04819438.5, dated Sep. 22, 2008, 2 pages.
Search Report issued in EP App. Ser. No. 04819438.5, dated Aug. 30, 2007, 3 pages.
Written Opinion issued for SG App. Ser. No. 200603436-7, dated Oct. 22, 2007, 6 pages.
Advisory Action issued in U.S. Appl. No. 10/580,989, dated May 27, 2010, 3 pages.
International Preliminary Report on Patentability issued in PCT App. Ser. No. PCT/JP2004/017574, dated Jul. 27, 2006, 4 pages.
Notice of Allowance issued in U.S. Appl. No. 10/580,989, dated Sep. 24, 2010, 7 pages.
Notice of Allowance issued in U.S. Appl. No. 10/580,989, dated Jan. 13, 2011, 5 pages.
Notice of Allowance issued in U.S. Appl. No. 10/580,989, dated Oct. 4, 2011, 6 pages.
Notice of Allowance issued in U.S. Appl. No. 10/580,989, dated Feb. 6, 2012, 7 pages.
Office Communication issued in EP App. Ser. No. 04819438.5, dated Jun. 13, 2008, 2 pages.
Submission Documents re Request for Continued Examination filed in U.S. Appl. No. 10/580,989, filed Feb. 8, 2011, 1 page.
Submission Documents re Request for Continued Examination filed in U.S. Appl. No. 10/580,989, filed Dec. 27, 2011, 1 page.
Request for Re-Examination and Amended Claims filed in CN App. Ser. No. 200480041020.8, filed Nov. 9, 2009, 13 pages (with English translation).
Response and Request for Continued Examination filed in U.S. Appl. No. 10/580,989, filed Dec. 17, 2010, 7 pages.
Response and Request for Continued Examination filed in U.S. Appl. No. 10/580,989, filed Jun. 10, 2010, 11 pages.
Response filed in CN App. Ser. No. 200480041020.8, filed Sep. 28, 2008, 15 pages (with English translation).
Restriction Requirement issued in U.S. Appl. No. 10/580,989, issued May 29, 2009, 4 pages.
International Preliminary Report on Patentability issued in PCT App. U.S. Appl. No. PCT/JP2007/058009 dated Nov. 27, 2008, 8 pages (English Translation).
Office Action in CN App. Ser. No. 200780021736.5, dated Nov. 4, 2010, 11 pages (with English translation).
European Search Report and Search Opinion in EP App. Ser. No. 07741445.6, dated Aug. 5, 2010, 6 pages.
Examination report in EP App. Ser. No. 07741445.6, dated Sep. 2, 2011, 5 pages.
Restriction Requirement in U.S. Appl. No. 12/296,915, dated Jan. 26, 2011, 12 pages.
Final Rejection in U.S. Appl. No. 12/296,915, dated Nov. 3, 2011, 6 pages.
International Preliminary Report on Patentability issued in PCT/JP2006/316249, on Feb. 20, 2008, 4 pages.
Office Action is SG App. Ser. No. 200700561-4, dated Mar. 6, 2008, 6 pages.
Office Action in JP App. Ser. No. 2006-524554, dated Mar. 7, 2007, 5 pages (English translation).
Office Action in EP App. Ser. No. 05766437.7, dated Mar. 16, 2007, 5 pages.
Response filed in EP App. Ser. No. 04819438.5, filed Jun. 23, 2008, 7 pages.
Response filed in U.S. Appl. No. 10/580,989, filed Jun. 29, 2009, 6 pages.
Office Action in IL App. Ser. No. 180782, dated Sep. 30, 2009, 3 pages (English translation).
Response filed in U.S. Appl. No. 12/296,915, dated Mar. 25, 2011, 9 pages.
Office Action in JP App. Ser. No. 2008-510971, dated Apr. 3, 2012, 6 pages (with English translation).
Argument filed in JP App. Ser. No. 2008-510971, dated May 22, 2012, 4 pages (with English translation).
Office Action in JP App. Ser. No. 2007-531040, dated Jul. 15, 2011, 7 pages.
Response filed in U.S. Appl. No. 10/580,989, filed Jan. 6, 2010, 9 pages.
Response filed in EP App. Ser. No. 07741445.6, dated Jan. 9, 2012, 14 pages.
Response filed in U.S. Appl. No. 12/296,915, dated Feb. 1, 2012, 4 pages.
Office Action in EP App. Ser. No. 05766437.7, dated Feb. 3, 2011, 5 pages.
Amendments filed in EP App. Ser. No. 07741445.6, dated Mar. 1, 2011, 40 pages.
Amendment filed in JP App. Ser. No. 2008-510971, dated Mar. 9, 2012, 23 pages (with English translation).
Response filed in SG App. Ser. No. 200603436-7, filed Mar. 19, 2008, 11 pages.
Office Action in CN App. Ser. No. 200780021736.5, dated May 25, 2011, 8 pages (with English translation).
Office Action in CN App. Ser. No. 200480041020.8, dated Jul. 4, 2008, 8 pages (with English translation).
Office Action in JP App. Ser. No. 2006-355330, dated Aug. 27, 2009, 6 pages (English translation).
Office Action in JP App. Ser. No. 2007-121660, dated Aug. 27, 2009, 7 pages (English translation).
Response filed in EP App. Ser. No. 04819438.5, filed Oct. 7, 2008, 14 pages.
Office Action in EP App. Ser. No. 05766437.7, dated Nov. 6, 2009, 4 pages.
Office Action in CA App. Ser. No. 2,574,177, dated Nov. 21, 2011, 5 pages.
Search Report in EP App. Ser. No. 05766437.7, dated Dec. 1, 2006, 10 pages.
Office Action in AU App. Ser. No. 2005264579, dated Dec. 9, 2009, 3 pages.
Office Action in KR App. Ser. No. 10-2007-7004164, dated Feb. 14, 2013, 8 pages (with English translation).
Response filed in EP App. Ser. No. 04819438.5, filed May 16, 2008, 35 pages.
Response filed in U.S. Appl. No. 10/580,989, filed May 18, 2010, 10 pages.
Response filed in U.S. Appl. No. 10/580,989, filed May 25, 2010, 6 pages.
Office Action in JP App. Ser. No. 2006-355330, dated Jun. 9, 2010, 7 pages (English translation).

(56) References Cited

OTHER PUBLICATIONS

Office Action in JP App. Ser. No. 2007-121660, dated Jun. 9, 2010, 4 pages (English translation).
Office Action in IL App. Ser. No. 180782, dated Oct. 10, 2010, 3 pages (English translation).
Office Action in IL App. Ser. No. 205193, dated Oct. 10, 2010, 4 pages (English translation).
Office Action in IL App. Ser. No. 205194, dated Oct. 10, 2010, 4 pages (English translation).
Office Action in IL App. Ser. No. 205195, dated Oct. 10, 2010, 4 pages (English translation).
Office Action in U.S. Appl. No. 12/296,915, dated Jun. 6, 2011, 9 pages.
Office Action in IL App. Ser. No. 180782, dated Mar. 26, 2012, 2 pages (English translation).
Office Action in IL App. Ser. No. 205193, dated Apr. 22, 2012, 2 pages (English translation).
Office Action in IL App. Ser. No. 205194, dated Feb. 17, 2013, 2 pages (English translation).
Office Action in CA App. Ser. No. 2649250, May 17, 2013, 4 pages.
Office Action in CN App. Ser. No. 200580031914.3, dated Jan. 16, 2009 (with English translation).
Office Action in JP App. Ser. No. 2008-510971, dated Jan. 10, 2012, 12 pages (with English translation).
Office Action in JP App. Ser. No. 2006-355330, dated Feb. 9, 2011, 2 pages (English translation).
Final Office Action in U.S. Appl. No. 10/580,989, dated Mar. 23, 2010, 12 pages.
Arguments filed in CN App. Ser. No. 200780021736.5, dated Mar. 21, 2011, 5 pages (with English translation).
Office Action in IN App. Ser. No. 744/DELNP/2007, dated Mar. 6, 2012, 2 pages (English translation).
Office Action in CN App. Ser. No. 200580031914.3, dated Mar. 9, 2011, 6 pages (with English translation).
Office Action in CN App. Ser. No. 200480041020.8, dated Mar. 9, 2011, 8 pages (with English translation).
Office Action in CN App. Ser. No. 200680038868.4, dated Apr. 5, 2012, 9 pages (with English translation).
Response filed in CN App. Ser. No. 200480041020.8, filed on May 24, 2011, 10 pages (with English translation).
Response filed in CN App. Ser. No. 200480041020.8, filed on May 27, 2010, 20 pages (with English translation).
Office Action in KR App. Ser. No. 10-2007-7004164, dated Jun. 1, 2012, 10 pages (with English translation).
Office Action in CN App. Ser. No. 200580031914.3, dated Aug. 21, 2009, 10 pages (with English translation).
Response filed in U.S. Appl. No. 12/296915, dated Sep. 6, 2011, 7 pages.
Office Action in JP App. Ser. No. 2006-524554, dated Nov. 1, 2006, 5 pages (English translation).
Argument filed in JP App. Ser. No. 2008-510971, dated Mar. 9, 2012, 14 pages (with English translation).
Amendment filed in JP App. Ser. No. 2008-510971, dated May 22, 2012, 23 pages (with English translation).
Office Action in EP App. Ser. No. 05766437.7, dated Oct. 4, 2012, 5 pages.
Office Action in U.S. Appl. No. 10/580,989, dated Oct. 9, 2009, 25 pages.
Office Action in CA App. Ser. No. 2,574,177, dated Dec. 4, 2012, 2 pages.
"Affymetrix GeneChip Human Genome U133 Array Set HG-U133A," Gene Expression Omnibus, Mar. 11, 2002, 2 pages.
"Affymetrix GeneChip Human Genome U95 Version [1 or 2] Set HG-U95A," Gene Expression Omnibus, Mar. 11, 2002, 2 pages.
Barberi et al., "Neural subtype specification of fertilization and nuclear transfer embryonic stem cells and application in Parkinsonian mice," Nature Biotechnology, Oct. 2003, 21(10):1200-07.
Bjorklund et al., "Embryonic stem cells develop into functional dopaminergic neurons after transplantation in a Parkinson rat model," PNAS: Proceedings of the National Academy of Sciences of the United States of America, Feb. 19, 2002, 99(4):2344-49.
Defer et al., "Long-term outcome of unilaterally transplanted Parkinsonian patients," Brain, 1996, 119:41-50.
EMBL GeneBank Accession No. AB013874, Nov. 16, 1998, 4 pages.
Failli et al., "Expression of the L1M-homeodomain gene Lmx1a (dreher) during development of the mouse nervous system," Mechanisms of Development, 2002, 118:225-228.
Freed et al., "Survival of implanted fetal dopamine cells and neurologic improvement 12 to 46 months after transplantation for Parkinson's disease," New Engl J Med., Nov. 26, 1992, 327(22): 1549-55.
Genbank accession AF226662 (Mar. 13, 2000), 2 pages.
GenBank Accession No. AF078166 (Jul. 30, 1998), 1 page.
Guillemot, "Vertebrate bHLH Genes and the Determination of Neuronal Fates," Experimental Cell Research, 1999, 253:357-364.
Holzschuh et al., "Dopamine transporter expression distinguishes dopaminergic neurons from other catecholaminergic neurons in the developing zebrafish embryo," Mechanisms of Development, 2001,101:237-243.
Hooper et al., "Localization of the mosaic transmembrane serine protease corin to heart myocytes," FEBS J, 2000, 267:6931-37.
Kawasaki et al., "Induction of Midbrain Dopaminergic Neurons from ES Cells by Stromal Cell-Derived Inducing Activity," Neuron, Oct. 2000, 28:31-40.
Kawasaki et al., "Generation of dopaminergic neurons and pigmented epithelia from primate ES cells by stromal cell-derived inducing activity," PNAS: Proceedings of the National Academy of Sciences of the United States of America, Feb. 5, 2002, 99(3):1580-85.
Kim et al. "Dopamine neurons derived from embryonic stem cells function in an animal model of Parkinson's disease," Nature, Jul. 4, 2002, 418:50-56.
Kitada and Serikawa, "Identification of the Causative Gene in the Tremor Rat by Positional Cloning," Proceedings of the 17th Annual Meeting of the Japanese Society of Animal Models for Human Diseases, 2001, pp. 6-10 (English Summary Only).
Kitada et al., "Truncation of LIM homeobox transcription factor Lmx1a results in abnormal development of the central nervous system of qc/qc rat," The 15th International Mouse Genome Conference, 2001, International Mammalian Genome Society, 1 page (Abstract Only).
Kordower et al., "Neuropathological evidence of graft survival and striatal reinnervation after the transplantation of fetal mesencephalic tissue in a patient with Parkinson's disease," New Engl J Med., Apr. 27, 1995, 332(17):1118-24.
Kruger et al., "The homeobox containing gene Lbx1 is required for correct dorsal-ventral patterning of the neural tube," J. Neurochem., 2002, 82(4):774-782.
Lee et al., "Efficient generation of midbrain and hindbrain neurons from mouse embryonic stem cells," Nature Biotechnology, Jun. 2000, 18(6):675-79.
Li et al., "Low-Density Lipoprotein Receptor Family," Molecular Neurobiology, Feb. 2001, 23(1):53-67.
Lindvall et al., "Human fetal dopamine neurons grafted into the striatum in two patients with severe Parkinson's disease," Archives of Neurology, Jun. 1989, 46(6):615-31.
Lopez-Lozano et al., "Regression of Parkinsonian fetal ventral Mesencephalon grafts upon withdrawal of Cyclosporine A immunosuppression," Transplantation Proceedings, Feb. 1997, 29(1-2):977-80.
Mazumder et al., "Translational control by the 3'-UTR: the ends specify the means," Trends in Biochemical Sciences, 2003, 28:91-98.
Millonig et al., "The mouse Dreher gene Lmx1a controls formation of the roof plate in the vertebrate CNS," Nature, Feb. 17, 2000, 403:764-769.
NCBI Accession No. AB013874, "Mus musculus mRNA for Low Density Lipoprotein Receptor Related Protein 4, complete cds," Nov. 11, 1998, 2 pages.

(56) References Cited

OTHER PUBLICATIONS

Okazaki et al., "Analysis of the mouse transcriptome based on functional annotation of 60,770 full-length cDNAs," Nature, Dec. 5, 2002, 420(6915):563-573.

Piccini et al., "Dopamine release from nigral transplants visualized in vivo in a Parkinson's patient," Nature Neuroscience, Dec. 1999, 2(12):1137-1140.

Schlegel, Dictionary of Plant Breeding, Second Edition, CRC Press, p. 191 (2009).

Sakamoto et al., "The candidate of cell surface marker of dopaminergic progenitor cells," The 27th Annual Meeting of the Molecular Biology Society of Japan, Nov. 2004, abstract 2PB-250, p. 762 (with English translation).

Sawamoto et al., "Generation of dopaminergic neurons in the adult brain from mesencephalic precursor cells labeled with a nestin-GFP transgene," J Neuroscience, Jun. 1, 2001, 21(11):3895-903.

Sawamoto et al., "Visualization, direct isolation, and transplantation of midbrain dopaminergic neurons," PNAS: Proceedings of the National Academy of Sciences of the United States of America, May 22, 2001, 98(11)6423-28.

Segev et al., "Nato3 is an evolutionarily conserved bHLH transcription factor expressed in the CNS of Drosophila and mouse," Mechanisms of Development, 2001, 106:197-202.

Selawry and Cameron, "Sertoli cell-enriched fractions in successful islet cell transplantation," Cell Transplantation, Mar.-Apr. 1993; 2(2):123-29 (Abstract Only).

Smidt et al., "A second independent pathway for development of mesencephalic dopaminergic neurons requires Lmx1b," Nature Neuroscience, 2000, 3:337-341.

Spencer et al., "Unilateral transplantation of human fetal mesencephalic tissue into the caudate nucleus of patients with Parkinson's disease," New Engl J Medicine, Nov. 26, 1992, 327(22):1541-48.

Studer et al., "Transplantation of expanded mesencephalic precursors leads to recovery in Parkinsonian rats," Nature Neuroscience, Aug. 1998, 1(4):290-95.

Thameem et al., "Cloning, expression and genomic structure of human LMX1A, and variant screening in Pima Indians," Gene, 2002, 290:217-225.

Tomita et al., "A Novel Low-Density Lipoprotein Receptor-Related Protein with Type II Membrane Protein-Like Structure Is Abundant in Heart," J Biochemistry, Oct. 1998, 124(4):784-789.

Verzi et al., "N-Twist, an Evolutionarily Conserved bHLH Protein Expressed in the Developing CNS, Functions as a Transcriptional Inhibitor," Developmental Biology, 2002, 249:174-190.

Wallen et al., "Transcriptional Control of Dopamine Neuron Development," Ann. N.Y. Acad. Sci., Jun. 1, 2003, 991:48-60.

Wernig et al., "Neurons derived from reprogrammed fibroblasts functionally integrate into the fetal brain and improve symptoms of rats with Parkinson's disease," Proc Natl Acad Sci U S A., Apr. 15, 2008, 105:5856-5861.

Widner et al., "Bilateral fetal mesencephalic grafting in two patients with Parkinsonism induced by 1-methyl-4-phenyl-1,2,3,6-tetrahydropyridine (MPTP)," New Engl J Medicine, Nov. 26, 1992, 327(22):1556-63.

Yan et al., "Corin, a Mosaic Transmembrane Serine Protease Encoded by a Novel cDNA from Human Heart," J Biological Chem., May 21, 1999, 274(21):14926-935.

Yoshizaki et al., "Isolation and transplantation of dopaminergic neurons generated from mouse embryonic stem cells," Neuroscience Letters, Jun. 3, 2004, 363(1):33-37.

Zhang et al., "Identification of Direct Serum-response Factor Gene Targets during $Me_2SO$-induced P19 Cardiac Cell Differentiation," J Biological Chem., 2005, 280(19):19115-19126.

Zhao et al., "Generation of embryonic stem cells and transgenic mice expressing green fluorescence protein in midbrain dopaminergic neurons," European J Neuroscience, Mar. 2004, 19(5):1133-1140.

Zigova et al., "Neuronal Progenitor Cells of the Neonatal Subventricular Zone Differentiate and Disperse Following Transplantation Into the Adult Rat Striatum" Cell Transplantation, Mar.-Apr. 1998, 7(2):137-156 (Abstract Only).

Partial Supplementary European Search Report in App. Ser. No. 12817048.7, dated Dec. 4, 2014, 7 pages.

DOI et al., "Isolation of Human Induced Pluripotent Stem Cell-Derived Dopaminergic Progenitors by Cell Sorting for Successful Transplantation," Stem Cell Reports, Mar. 11, 2014, 2(3):337-350.

Lopezjimenez et al., "Examination of FGFRL1 as a candidate gene for diaphragmatic defects at chromosome 4p16.3 shows that Fgfrl1 null mice have reduced expression of Tpm3, sarcomere genes and Lrtm1 in the diaphragm," Hum Genet., Dec. 19, 2009, 127:325-336.

Extended European Search Report issued in corresponding EP Application Ser. No. 12817048.7, dated Mar. 31, 2015, 10 pages.

Office Action issued in European Application No. 12817048.7, dated Jan. 11, 2016, 5 pages.

Edman, L.C. et al. 2008 "The beta-chemokines CCL2 and CCL7 are two novel differentiation factors for midbrain dopaminergic precursors and neurons," *Experimental Cell Research* 314:10; 2123-30.

Response to EP Search Report for EP Application No. 12817048.7, filed Oct. 16, 2015, 8 pages.

Response to Office Action in EP Application No. 12817048.7, filed May 23, 2016, 7 pages.

Office Action issued in European Application No. 12817048.7, dated Jun. 7, 2016, 4 pages.

Office Action issued in Japanese Application No. 2014-502915, dated Jul. 19, 2016, 9 pages, with English translation.

\* cited by examiner

A: Day 0 after sorting

B: Day 7 after sorting

A: Day 0 after sorting

B: Day 7 after sorting

SEQUENCE LISTING

```
<160> NUMBER OF SEQ ID NOS: 2

<210> SEQ ID NO 1
<211> LENGTH: 294
<212> TYPE: PRT
<213> ORGANISM: Artificial Sequence
<220> FEATURE:
<223> OTHER INFORMATION: Protein fragment

<400> SEQUENCE: 1

Met Leu Asn Glu Gly Leu Cys Cys Gly Ala Trp Ala Met Lys Gly Thr
1               5                   10                  15

Leu Leu Leu Val Ser Ser Val Gly Leu Leu Pro Gly Val Gly Ser
            20                  25                  30

Cys Pro Met Lys Cys Leu Cys His Pro Ser Ser Asn Ser Val Asp Cys
        35                  40                  45

Ser Gly Gln Gly Leu Ser Lys Val Pro Arg Asp Leu Pro Pro Trp Thr
    50                  55                  60

Val Thr Leu Leu Leu Gln Asp Asn Arg Ile His Trp Leu Pro Ala Leu
65                  70                  75                  80

Ala Phe Gln Ser Val Ser Leu Leu Ser Thr Leu Asn Leu Ser Asn Asn
                85                  90                  95
```

```
Ser Leu Ser Asn Leu Ala Ala Glu Ala Phe Tyr Gly Leu Pro His Leu
                100                 105                 110

Arg Val Leu Asn Val Thr Gln Asn Ser Leu Leu Ser Ile Glu Ser Ser
            115                 120                 125

Phe Ala His Ala Leu Pro Gly Leu Arg Glu Leu Asp Leu Ser Ser Asn
        130                 135                 140

Ser Leu Arg Ile Leu Pro Thr Ser Leu Gly Lys Pro Trp Glu Asn Leu
145                 150                 155                 160

Thr Val Phe Ala Val Gln Gln Asn His Leu Leu His Leu Asp Arg Glu
                165                 170                 175

Leu Leu Glu Ala Met Pro Lys Val Arg Leu Val Leu Leu Lys Asp Asn
            180                 185                 190

Pro Trp Ile Cys Asp Cys His Leu Leu Gly Leu Lys Leu Trp Leu Glu
        195                 200                 205

Arg Phe Thr Phe Gln Gly Gly Glu Thr Asp Gly Ala Ile Cys Arg Leu
    210                 215                 220

Pro Glu Pro Trp Gln Gly Lys Ala Leu Leu Ser Ile Pro His Glu Leu
225                 230                 235                 240

Tyr Gln Pro Cys Ser Leu Pro Ser Gln Asp Leu Ala Pro Ser Leu Val
                245                 250                 255

Gln Gln Pro Gly Ser Ala Pro Gln Asp Ala Gln Lys Ser His Glu Asn
            260                 265                 270

Ser Ser Gly Gln Gln Asp Pro Leu Glu Cys Glu Ala Lys Pro Lys Pro
        275                 280                 285

Lys Pro Thr Asn Leu Arg
    290

<210> SEQ ID NO 2
<211> LENGTH: 283
<212> TYPE: PRT
<213> ORGANISM: Artificial Sequence
<220> FEATURE:
<223> OTHER INFORMATION: protein fragment

<400> SEQUENCE: 2

Met Lys Gly Glu Leu Leu Phe Ser Ser Val Ile Val Leu Leu Gln
1               5                   10                  15

Val Val Cys Ser Cys Pro Asp Lys Cys Tyr Cys Gln Ser Ser Thr Asn
                20                  25                  30

Phe Val Asp Cys Ser Gln Gln Gly Leu Ala Glu Ile Pro Ser His Leu
            35                  40                  45

Pro Pro Gln Thr Arg Thr Leu His Leu Gln Asp Asn Gln Ile His His
    50                  55                  60

Leu Pro Ala Phe Ala Phe Arg Ser Val Pro Leu Met Thr Leu Asn Leu
65                  70                  75                  80

Leu Ser Asn Asn Ser Leu Ser Asn Leu Ala Pro Gly Ala Phe His Gly
                85                  90                  95

Leu Gln His Leu Gln Val Leu Asn Leu Thr Gln Asn Ser Leu Leu Ser
            100                 105                 110

Leu Glu Ser Arg Leu Phe His Ser Leu Pro Gln Leu Arg Glu Leu Asp
        115                 120                 125

Leu Ser Ser Asn Asn Ile Ser His Leu Pro Thr Ser Leu Gly Glu Thr
    130                 135                 140

Trp Glu Asn Leu Thr Ile Leu Ala Val Gln Gln Asn Gln Leu Gln Gln
145                 150                 155                 160
```

-continued

```
Leu Asp Arg Ala Leu Leu Glu Ser Met Pro Ser Val Arg Leu Leu Leu
            165                 170                 175

Leu Lys Asp Asn Leu Trp Lys Cys Asn Cys His Leu Leu Gly Leu Lys
            180                 185                 190

Leu Trp Leu Glu Lys Phe Val Tyr Lys Gly Gly Leu Thr Asp Gly Ile
        195                 200                 205

Ile Cys Glu Ser Pro Asp Thr Trp Lys Gly Lys Asp Leu Leu Arg Ile
        210                 215                 220

Pro His Glu Leu Tyr Gln Pro Cys Pro Leu Pro Ala Pro Asp Pro Val
225                 230                 235                 240

Ser Ser Gln Ala Gln Trp Pro Gly Ser Ala His Gly Val Val Leu Arg
            245                 250                 255

Pro Pro Glu Asn His Asn Ala Gly Glu Arg Glu Leu Leu Glu Cys Glu
            260                 265                 270

Leu Lys Pro Lys Pro Arg Pro Ala Asn Leu Arg
        275                 280
```

MARKERS FOR DOPAMINERGIC NEURON PROGENITOR CELLS

RELATED APPLICATIONS

This application is the U.S. National Phase under 35 U.S.C. §371 of International Application PCT/JP2012/069785, filed Jul. 27, 2012, which claims priority to U.S. Provisional Patent Application No. 61/512,162, filed Jul. 27, 2011.

REFERENCE TO SEQUENCE LISTING

This application incorporates by reference the sequence listing submitted as ASCII text filed via EFS-Web on Jan. 21, 2014. The Sequence Listing is provided as a file entitled "2014-01-20 SEQ LST-TOYA194.001APC," created on Jan. 22, 2014, and which is approximately 5.16 kilobytes in size.

BACKGROUND ART

Parkinson's disease is a neurodegenerative disease caused by loss of dopaminergic neural cells in the mesencephalic substantia nigra, and about 4 million people in the world are currently suffering from this disease. For treatment of Parkinson's disease, pharmacotherapy with L-dopa or a dopamine agonist; the coagulation method or deep brain stimulation by stereotaxy; fetal mesencephalic grafting; or the like has been carried out.

Fetal mesencephalic grafting is problematic from an ethical point of view because of its source of supply, and the risk of infection is high in this treatment. Thus, a therapeutic method using neural cells induced from pluripotent stem cells such as embryonic stem cells (ES cells) or induced pluripotent stem cells (iPS cells) has been proposed (Wernig M, et al., Proc Natl Acad Sci USA. 2008, 105: 5856-5861). However, the possibility of formation of a benign tumor after transplantation of induced neural cells has been pointed out, thus, selection of safe cells that can survive has been demanded for the transplantation.

In view of this, genes that can be used as markers for dopaminergic neural cells and/or dopaminergic neuron progenitor cells have been reported (WO2005/052190, WO 2006/009241 and WO 2007/119759), but it is considered that more markers are necessary for restrictive extraction of specific cells suitable for transplantation.

SUMMARY OF THE INVENTION

The present invention aims to extract dopaminergic neuron progenitor cells from a cell population comprising dopaminergic neuron progenitor cells. Therefore, an object of the present invention is to provide markers specific for dopaminergic neuron progenitor cells.

In order to solve the above-described object, the inventors of the present invention focused attention on corin, which is a cell surface membrane protein that has been considered to be a marker of dopaminergic neuron progenitor cells, and extracted corin-positive cells from a cell population comprising neural progenitor cells or neural cells produced by differentiation induction from pluripotent stem cells. The inventors then discovered genes and glycolipids as cell surface markers specifically expressed in these cells, and confirmed that dopaminergic neuron progenitor cells can be obtained by using these markers as indices, thereby completed the present invention.

An aspect of the present invention is to provide a method for producing dopaminergic neuron progenitor cells, said method comprising:

extracting dopaminergic neuron progenitor cells from a cell population comprising dopaminergic neuron progenitor cells by using as an index/indices the positivity/positivities of any one or more of markers selected from the group consisting of CD15 (SSEA-1), CD24, CD46, CD47, CD49b, CD57, CD58, CD59, CD81, CD90, CD98, CD147, CD184, Disalogangliosid GD2, SSEA-4, CD49f, SERINC4, CCR9, PHEX, TMPRSS11E, HTR1E, SLC25A2, Ctxn3, Ccl7, Chrnb4, Chrna3, Kcnv2, Grm2, Syt2, Lim2, Mboat1, St3gal6, Slc39a12, Tacr1, Lrtm1 and Dscam, and/or the negativity of CD201.

Another aspect of the present invention is to provide the method as described above, wherein the positive marker is Lrtm1.

Another aspect of the present invention is to provide the method as described above, wherein said step of extracting dopaminergic neuron progenitor cells further uses as an index/indices the positivity/positivities of corin and/or Lmx1a.

Another aspect of the present invention is to provide the method as described above, wherein said dopaminergic neuron progenitor cells are human dopaminergic neuron progenitor cells.

Another aspect of the present invention is to provide the method as described above, wherein said cell population comprising dopaminergic neuron progenitor cells is a cell population whose differentiation was induced from pluripotent stem cells, or a cell population composed of cells of an isolated tissue(s).

Another aspect of the present invention is to provide the method as described above, wherein said cell population whose differentiation was induced from pluripotent stem cells is a cell population obtained by culturing pluripotent stem cells in a medium supplemented with a BMP inhibitor and a TGFβ inhibitor.

Another aspect of the present invention is to provide a method for detecting dopaminergic neuron progenitor cells in a cell population comprising dopaminergic neuron progenitor cells, said method comprising detecting dopaminergic neuron progenitor cells using as an index/indices the positivity/positivities of any one or more of markers selected from the group consisting of CD15 (SSEA-1), CD24, CD46, CD47, CD49b, CD57, CD58, CD59, CD81, CD90, CD98, CD147, CD184, Disalogangliosid GD2, SSEA-4, CD49f, SERINC4, CCR9, PHEX, TMPRSS11E, HTR1E, SLC25A2, Ctxn3, Ccl7, Chrnb4, Chrna3, Kcnv2, Grm2, Syt2, Lim2, Mboat1, St3gal6, Slc39a12, Tacr1, Lrtm1 and Dscam, and/or the negativity of CD201.

Another aspect of the present invention is to provide the method as described above, wherein the positive marker is Lrtm1.

Another aspect of the present invention is to provide the method as described above, wherein said step of detecting dopaminergic neuron progenitor cells further uses as an index/indices the positivity/positivities of corin and/or Lmx1a.

Another aspect of the present invention is to provide the method as described above, wherein said dopaminergic neuron progenitor cells are human dopaminergic neuron progenitor cells.

Another aspect of the present invention is to provide the method as described above, wherein said cell population comprising dopaminergic neuron progenitor cells is a cell population whose differentiation was induced from pluripotent stem cells, or a cell population composed of cells of an isolated tissue(s).

Another aspect of the present invention is to provide the method as described above, wherein said cell population whose differentiation was induced from pluripotent stem cells is a cell population obtained by culturing pluripotent stem cells in a medium supplemented with a BMP inhibitor and a TGFβ inhibitor.

Another aspect of the present invention is to provide a kit for detecting dopaminergic neuron progenitor cells, comprising a reagent(s) for detecting any one or more of markers selected from the group consisting of CD15 (SSEA-1), CD24, CD46, CD47, CD49b, CD57, CD58, CD59, CD81, CD90, CD98, CD147, CD184, Disalogangliosid GD2, SSEA-4, CD49f, SERINC4, CCR9, PHEX, TMPRSS11E, HTR1E, SLC25A2, Ctxn3, Ccl7, Chmb4, Chma3, Kcnv2, Grm2, Syt2, Lim2, Mboat1, St3gal6, Slc39a12, Tacr1, Lrtm1, Dscam and CD201.

Another aspect of the present invention is to provide the kit as described above, wherein said reagent(s) is/are an antibody/antibodies.

Another aspect of the present invention is to provide the kit as described above, wherein the antibody is anti-Lrtm1 antibody which recognized an extracellular domain of Lrtm1.

Another aspect of the present invention is to provide a therapeutic agent for Parkinson's disease, comprising dopaminergic neuron progenitor cells produced by the method as described above.

BRIEF DESCRIPTION OF THE DRAWINGS

FIG. 1A shows the image of mouse Lrtm1 positive and negative cells just after sorting. Lmx1a, DAPI and Corin are shown in red, blue and green, respectively. FIG. 1B shows the image of mouse Lrtm1 positive and negative cells at 7 days after sorting. In the left panel TH and DAPI are shown in green and blue, in the second panel from left TH and Tuj1 are shown in green and white, in the third panel from left Nurr1 and TH are shown in red and green, and in right panel DAT and DAPI are shown in green and blue, respectively.

FIG. 3A shows the image of human LRTM1 positive and negative cells just after sorting. LMX1a, DAPI and CORN are shown in red, blue and green, respectively. FIG. 3B shows the image of human LRTM1 positive and negative cells at 7 days after sorting. LMX1a, DAPI, NURR1 and TH are shown in red, blue, white and green, respectively.

DESCRIPTION OF THE EMBODIMENTS OF THE INVENTION

Figure 1:
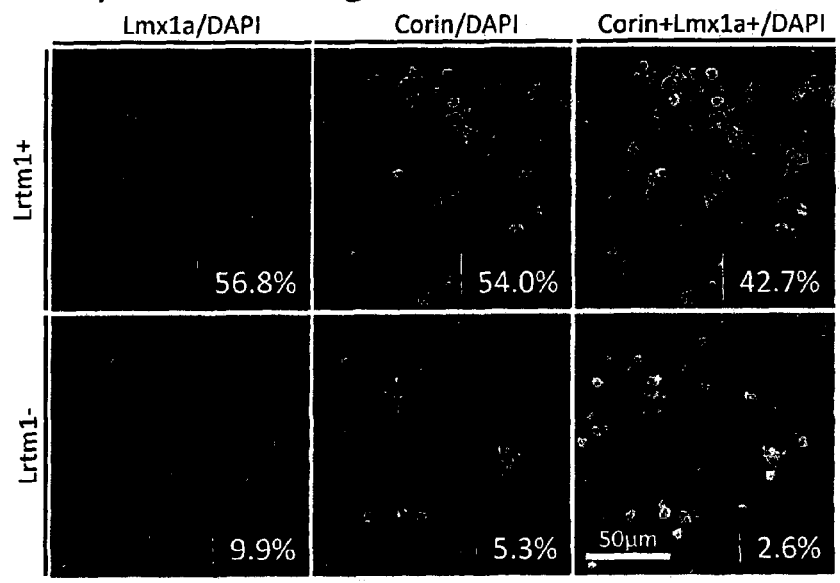
FIG. 1 shows fluorescent image for immunostaining (photograph).
Figure 1:
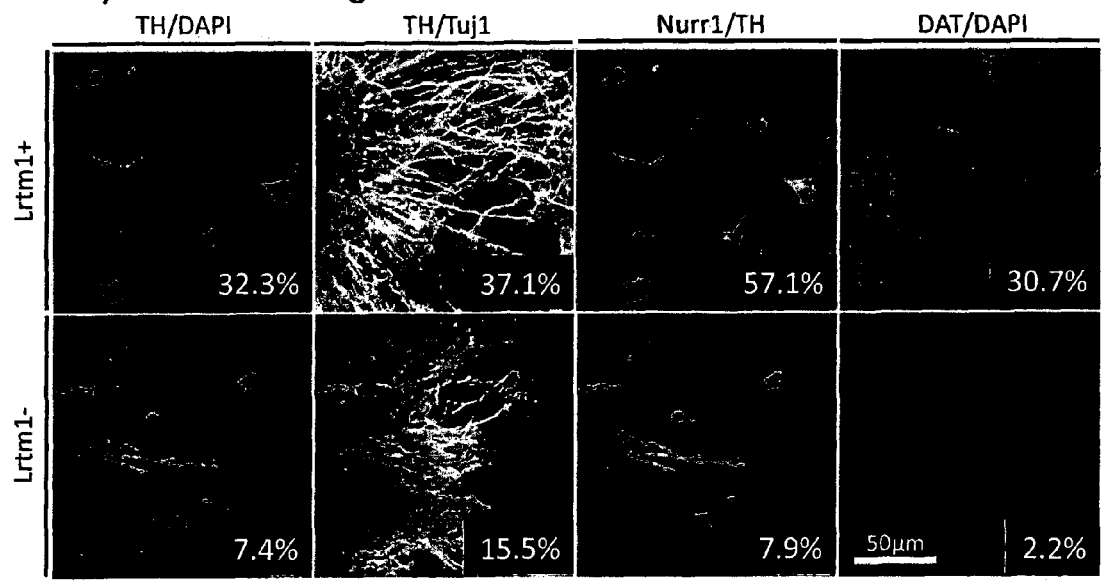

The present invention will now be described below detail.
The present invention relates to:
a method for producing dopaminergic neuron progenitor cells, the method comprising: extracting dopaminergic neuron progenitor cells from a cell population comprising dopaminergic neuron progenitor cells by using as an index/indices the positivity/positivities of any one or more of markers selected from the group consisting of CD15 (SSEA-1), CD24, CD46, CD47, CD49b, CD57, CD58, CD59, CD81, CD90, CD98, CD147, CD184, Disalogangliosid GD2, SSEA-4, CD49f, SERINC4, CCR9, PHEX, TMPRSS11E, HTR1E, SLC25A2, Ctxn3, Ccl7, Chmb4, Chma3, Kcnv2, Grm2, Syt2, Lim2, Mboat1, St3gal6, Slc39a12, Tacr1, Lrtm1 and Dscam, and/or the negativity of CD201; and a method for detecting dopaminergic neuron progenitor cells in a cell population comprising dopaminergic neuron progenitor cells, the method comprising detecting dopaminergic neuron progenitor cells using as an index/indices the positivity/positivities of any one or more of markers selected from the group consisting of CD15 (SSEA-1), CD24, CD46, CD47, CD49b, CD57, CD58, CD59, CD81, CD90, CD98, CD147, CD184, Disalogangliosid GD2, SSEA-4, CD49f, SERINC4, CCR9, PHEX, TMPRSS11E, HTR1E, SLC25A2, Ctxn3, Ccl7, Chmb4, Chma3, Kcnv2, Grm2, Syt2, Lim2, Mboat1, St3gal6, Slc39a12, Tacr1, Lrtm1 and Dscam, and/or the negativity of CD201.

In the present invention, the term "dopaminergic neuron progenitor cells" means cells which are characterized in that they are positive for at least one of corin (WO2006/009241) and Lmx1a (WO2005/052190)) and which become dopaminergic neural cells after maturation. The dopaminergic neural cells are not restricted, and may be characterized in that they are positive for tyrosine hydroxylase (TH). However, in the present invention, dopaminergic neuron progenitor cells and dopaminergic neural cells are not clearly distinguished from each other, and TH-positive cells can also be said to be dopaminergic neuron progenitor cells.

In the present invention, the origin of the cell population comprising dopaminergic neuron progenitor cells is not restricted as long as the cell population is a population of cells comprising dopaminergic neuron progenitor cells. For example, the origin may be a cell population contained in a tissue obtained by an arbitrary method, or a cell line established from a tissue. The tissue herein is a brain tissue, preferably fetal midbrain. The cell population may also be a cell population comprising neural progenitor cells obtained by differentiation induction of bone marrow stromal cells (Dezawa M, et al., J Clin Invest 2004, 113: 1701-1710) or pluripotent stem cells, or a cell population comprising neural progenitor cells directly induced from fibroblasts (Vierbuchen T, et al., Nature. 2010, 463:1035-1041).

In the present invention, the term "extraction of dopaminergic neuron progenitor cells" means to increase the ratio of dopaminergic neuron progenitor cells relative to the ratios of other types of cells, and preferably means to concentrate dopaminergic neuron progenitor cells to a content of not less than 50%, not less than 60%, not less than 70%, not less than 80% or not less than 90%. The above term more preferably means to obtain a cell population which comprises dopaminergic neuron progenitor cells at a content of 100%.

The markers to be used in the present invention, CD15 (SSEA-1), CD24, CD46, CD47, CD49b, CD57, CD58, CD59, CD81, CD90, CD98, CD147, CD184, Disalogangliosid GD2, SSEA-4, CD49f, SERINC4, CCR9, PHEX, IMPRSS11E, HTR1E, SLC25A2, Ctxn3, Ccl7, Chmb4, Chma3, Kcnv2, Grm2, Syt2, Lim2, Mboat1, St3gal6, Sk39a12, Tacr1, Lrtm1, Dscam and CD201, include the polynucleotides represented by the NCBI accession numbers described in Table 1 and proteins encoded thereby, and transcriptional variants, splicing variants, homologues and fragments thereof. The fragments herein preferably correspond to extracellular domains of the markers, in consideration of the fact that the markers are used for recognition of cells. In this invention, preferable marker is Lrtm1. More preferably, the marker is the fragment of extracellular domain of Lrtm1. The marker can be used together with conventional marker(s), such as corin (WO2006/009241), Lmx1a (WO2005/052190), 65B13 (WO2004/038018) and 185A5 (WO2007/119759).

TABLE 1

| Marker | NCBI Accession number | |
|---|---|---|
| | Mouse | Homo sapiens |
| CD15 (SSEA-1) | NM_010242 | NM_002033 |
| CD24 | NM_009846 | NM_013230 |
| CD46 | NM_010778 | NM_002389 |
| | | NM_153826 |
| | | NM_172350 |
| | | NM_172351 |
| | | NM_172352 |
| | | NM_172353 |
| | | NM_172359 |
| | | NM_172361 |
| CD47 | NM_010581 | NM_001777 |
| | | NM_198793 |
| CD49b | NM_008396 | NM_002203 |
| CD57 | NM_029792 | NM_018644 |
| | | NM_054025 |
| CD58 | — | NM_001779 |
| | | NM_001144822 |
| CD59 | NM_001111060 | NM_203330 |
| | NM_007652 | NM_000611 |
| | | NM_203329 |
| | | NM_203331 |
| | | NM_001127223 |
| | | NM_001127225 |
| | | NM_001127226 |
| | | NM_001127227 |
| CD81 | NM_133655 | NM_004356 |
| CD90 | NM_009382 | NM_006288 |
| CD98 | NM_001161413 | NM_001012662 |
| (SLC3A2, SLC7A5) | NM_008577 | NM_002394 |
| | NM_011404 | NM_001012664 |
| | | NM_001013251 |
| | | NM_003486 |
| CD147 | NM_001077184 | NM_001728 |
| | NM_009768 | NM_198589 |
| | | NM_198591 |
| CD184 | NM_009911 | NM_001008540 |
| | | NM_003467 |
| CD49f | NM_008397 | NM_000210 |
| | | NM_001079818 |
| CD201 | NM_011171 | NM_006404 |
| SERINC4 | NM_001025371 | NM_001033517 |
| CCR9 | NM_001166625 | NM_006641 |
| | NM_009913 | NM_031200 |
| PHEX | NM_011077 | NM_000444 |
| TMPRSS11E | NM_172880 | NM_014058 |
| HTR1E | — | NM_000865 |
| SLC25A2 | NM_001159275 | NM_031947 |
| Ctxn3 | NM_001134697 | NM_001048252 |
| | | NM_001127385 |
| Ccl7 | NM_013654 | NM_006273 |
| Chrnb4 | NM_148944 | NM_000750 |
| Chrna3 | NM_145129 | NM_000743 |
| | | NM_001166694 |
| Kcnv2 | NM_183179 | NM_133497 |
| Grm2 | NM_001160353 | NM_000839 |
| | | NM_001130063 |
| Syt2 | NM_009307 | NM_001136504 |
| | | NM_177402 |
| Lim2 | NM_177693 | NM_001161748 |
| | | NM_030657 |
| Mboat1 | NM_153546 | NM_001080480 |
| St3gal6 | NM_018784 | NM_006100 |
| Slc39a12 | NM_001012305 | NM_001145195 |
| Tacr1 | NM_009313 | NM_001058 |
| | | NM_015727 |
| Lrtm1 | NM_176920 | NM_020678 |
| Dscam | NM_031174 | NM_001389 |

Disalogangliosid GD2 and SSEA-4, which are used as markers, are glycolipids. Disalogangliosid GD2 is a sphingoglycolipid which is represented as Cer-Glc-Gal(NeuAc-NeuAc)-GalNAc, wherein Cer represents ceramide, Glc represents glucopyranose, Gal represents galactopyranose, NeuAc represents acetylneuramic acid, and GalNAc represents acetylgalactopyranose. SSEA-4 is a sphingoglycolipid having sialosyl-galactosyl-globoside (sialosyl-Gb5) as an epitope.

<Pluripotent Stem Cells>

In cases where a cell population comprising dopaminergic neuron progenitor cells is prepared by differentiation of pluripotent stem cells, the pluripotent stem cells have pluripotency which enables the cells to differentiate into any cells existing in the living body, and also have growth ability. Examples of the pluripotent stem cells include, but are not limited to, embryonic stem (ES) cells, embryonic stem cells derived from a cloned embryo obtained by nuclear transfer ("ntES cells"), germline stem cells ("GS cells"), embryonic germ cells ("EG cells"), induced pluripotent stem (iPS) cells, and pluripotent cells derived from cultured fibroblasts and bone marrow stem cells (Muse cells). The pluripotent stem cells are preferably ES cells, ntES cells or iPS cells.

(A) Embryonic Stem Cells

ES cells are stem cells established from the inner cell mass of an early embryo (for example, blastocyst) of a mammal such as human or mouse, which cells have pluripotency and growth ability by self-renewal.

ES cells are stem cells originated from the inner cell mass of a blastocyst which is the embryo formed following the 8-cell stage and the morula stage of a fertilized egg, and ES cells have ability to differentiate into any cells constituting an adult, that is, the so called pluripotency of differentiation, and growth ability by self-renewal. ES cells were discovered in mouse in 1981 (M. J. Evans and M. H. Kaufman (1981), Nature 292:154-156), and followed by establishment of ES cell lines of primates such as human and monkey (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by removing the inner cell mass from the blastocyst of a fertilized egg of a subject animal, followed by culturing the inner cell mass on fibroblasts as feeders. The cells can be maintained by subculturing using a medium supplemented with a substance(s) such as leukemia inhibitory factor (LIF) and/or basic fibroblast growth factor (bFGF). Methods of establishment and maintenance of human and monkey ES cells are described in, for example, U.S. Pat. No. 5,843,780 B; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103: 9554-9559; H. Suemori et al. (2001), Dev. Dyn., 222:273-279; H. Kawasaki et al. (2002), Proc. Natl. Acad. Sci. USA, 99:1580-1585; and Klimanskaya I, et al. (2006), Nature. 444:481-485.

In terms of the medium for preparation of ES cells, human ES cells can be maintained, for example, using DMEM/F-12 medium supplemented with 0.1 mM 2-mercaptoethanol, 0.1 mM non-essential amino acids, 2 mM L-glutamic acid, 20% KSR and 4 ng/ml bFGF at 37° C. under a moist atmosphere of 2% $CO_2$/98% air (O. Fumitaka et al. (2008), Nat. Biotechnol., 26:215-224). Further, ES cells need to be subcultured every 3 to 4 days, and the subculture can be carried out using 0.25% trypsin and 0.1 mg/ml collagenase IV in PBS supplemented with 1 mM CaCl$_2$ and 20% KSR.

Selection of ES cells can be generally carried out by the Real-Time PCR method using as an index/indices expression of a gene marker(s) such as alkaline phosphatase, Oct-3/4 and/or Nanog. In particular, for selection of human ES cells, expression of a gene marker(s) such as OCT-3/4, NANOG and/or ECAD can be used as an index/indices (E. Kroon et al. (2008), Nat. Biotechnol., 26:443-452).

In terms of human ES cell lines, for example, WA01(H1) and WA09(H9) can be obtained from WiCell Research Institute, and KhES-1, KhES-2 and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similarly to ES cells, these cells can be induced to differentiate into various series of cells, and, for example, have a property to enable preparation of a chimeric mouse by transplantation of the cells to a mouse blastocyst (M. Kanatsu-Shinohara et al. (2003) Biol. Reprod., 69:612-616; K. Shinohara et al. (2004), Cell, 119:1001-1012). Germline stem cells are capable of self-renewal in a medium containing glial cell line-derived neurotrophic factor (GDNF), and, by repeating subculture under the same culture conditions as those for ES cells, germline stem cells can be obtained (Masanori Takehashi et al. (2008), Experimental Medicine, 26(5) (extra edition):41-46, Yodosha (Tokyo, Japan)).

(C) Embryonic Germ Cells

Embryonic germ cells are established from fetal primordial germ cells and have pluripotency similarly to ES cells. They can be established by culturing primordial germ cells in the presence of substances such as LIF, bFGF and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be prepared by introducing specific reprogramming factors to somatic cells, which reprogramming factors are in the form of DNA or protein. iPS cells are somatic cell-derived artificial stem cells having properties almost equivalent to those of ES cells, such as pluripotency of differentiation and growth ability by self-renewal (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666). The reprogramming factors may be constituted by genes or gene products thereof, or non-coding RNAs, which are expressed specifically in ES cells; or genes or gene products thereof, non-coding RNAs or low molecular weight compounds, which play important roles in maintenance of the undifferentiated state of ES cells. Examples of the reprogramming factors include Oct3/4, Sox2, Sox1, Sox3, Sox15, Sox17, Klf4, Klf2, c-Myc, N-Myc, L-Myc, Nanog, Lin28, Fbxl 5, ERas, ECAT15-2, Tcl1, beta-catenin, Lin28b, Sall1, Sall4, Esrrb, Nr5a2, Tbx3 and Glis1, and these reprogramming factors may be used either alone or in combination. Examples of the combinations of the reprogramming factors include those described in WO2007/069666; WO2008/118820; WO2009/007852; WO2009/032194; WO2009/058413; WO2009/057831; WO2009/075119; WO2009/079007; WO2009/091659; WO2009/101084; WO2009/101407; WO2009/102983; WO2009/114949; WO2009/117439; WO2009/126250; WO2009/126251; WO2009/126655; WO2009/157593; WO2010/009015; WO2010/033906; WO2010/033920; WO2010/042800; WO2010/050626; WO 2010/056831; WO2010/068955; WO2010/098419; WO2010/102267; WO 2010/111409; WO 2010/111422; WO2010/115050; WO2010/124290; WO2010/147395; WO2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat. Biotechnol. 26:1269-1275; Sin Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat Cell Biol. 11:197-203; R. L. Judson et al., (2009), Nat. Biotech., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6:167-74; Han J, et al. (2010), Nature. 463:1096-100; Mali P, et al. (2010), Stem Cells. 28:713-720; and Maekawa M, et al. (2011), Nature. 474: 225-9.

Examples of the above-described reprogramming factors also include histone deacetylase (HDAC) inhibitors [for example, low molecular weight inhibitors such as valproic acid (VPA), trichostatin A, sodium butyrate, MC 1293 and M344; and nucleic acid-type expression inhibitors such as siRNAs and shRNAs against HDAC (e.g., HDAC 1 siRNA Smartpool® (Millipore) and HUSH 29mer shRNA Constructs against HDAC 1 (OriGene))], MEK inhibitors (for example, PD184352, PD98059, U0126, SL327 and PD0325901), Glycogen synthase kinase-3 inhibitors (for example, Bio and CHIR99021), DNA methyltransferase inhibitors (for example, 5'-azacytidine), histone methyltransferase inhibitors (for example, low molecular weight inhibitors such as BIX-01294; and nucleic acid-type expression inhibitors such as siRNAs and shRNAs against Suv39h1, Suv39h2, SetDB1 and G9a), L-channel calcium agonists (for example, Bayk8644), butyric acid, TGFβ inhibitors or ALK5 inhibitors (for example, LY364947, SB431542, 616453 and A-83-01), p53 inhibitors (for example, siRNAs and shRNAs against p53), ARID3A inhibitors (for example, siRNAs and shRNAs against ARID3A), miRNAs such as miR-291-3p, miR-294, miR-295 and mir-302, Wnt Signaling (for example, soluble Wnt3a neuropeptide Y, prostaglandins (for example, prostaglandin E2 and prostaglandin J2), hTERT, SV40LT, UTF1, IRX6, GLISI, PITX2 and DMRTB1, which are employed for enhancing the establishment efficiency, and, in the present description, these factors employed for the purpose of enhancement of the establishment efficiency are not particularly distinguished from the above-described reprogramming factors.

In cases where the reprogramming factors are in the form of protein, the reprogramming factors may be introduced into somatic cells by a method such as lipofection, fusion with a cell membrane-permeable peptide (e.g., HIV-derived TAT or polyarginine), or microinjection.

In cases where the reprogramming factors are in the form of DNA, the reprogramming factors may be introduced into somatic cells by a method such as use of a vector including virus, plasmid and artificial chromosome vectors; lipofection; use of liposome; or microinjection. Examples of the virus vectors include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors and Sendai virus vectors (WO 2010/008054). Examples of the artificial chromosome vectors include human artificial chromosomes (HACs), yeast artificial chromosomes (YACs), and bacterial artificial chromosomes (BACs and PACs). Examples of the plasmids include plasmids for mammalian cells (Science, 322:949-953, 2008). The vectors may contain a regulatory sequence(s) such as a promoter, enhancer, ribosome binding sequence, terminator and/or polyadenylation site; and, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG; and/or the like to enable expression of the nuclear reprogramming factors. Further, in order to remove, after introduction of the above vector into somatic cells, the genes encoding the reprogramming factors, or both the promoters and the genes encoding the reprogramming factors linked thereto, the vector may have LoxP sequences upstream and downstream of these sequences.

Further, in cases where the reprogramming factors are in the form of RNA, each reprogramming factor may be introduced into somatic cells by a method such as lipofection or microinjection, and an RNA into which 5-methylcytidine and pseudouridine (TriLink Biotechnologies) were incorporated may be used in order to suppress degradation (Warren L, (2010) Cell Stem Cell. 7:618-630).

Examples of the medium for induction of the iPS cells include the DMEM, DMEM/F12 and DME media supplemented with 10 to 15% FBS (these media may further contain LIF, penicillin/streptomycin, puromycin, L-glutamine, non-essential amino acids, β-mercaptoethanol and/or the like, as appropriate); and commercially available media [for example, a medium for culturing mouse ES cells (TX-WES medium, Thromb-X), medium for culturing primate ES cells (medium for primate ES/iPS cells, ReproCELL) and serum-free medium (mTeSR, Stemcell Technology)].

Examples of the culture method include a method wherein somatic cells and reprogramming factors are brought into contact with each other at 37° C. in the presence of 5% $CO_2$ in DMEM or DMEM/F12 medium supplemented with 10% FBS, and the cells are cultured for about 4 to 7 days, followed by plating the cells on feeder cells (e.g., mitomycin C-treated STO cells or SNL cells) and starting culture in a bFGF-containing medium for culturing primate ES cells about 10 days after the contact between the somatic cells and the reprogramming factors, thereby allowing iPS-like colonies to appear about 30 to about 45 days after the contact, or later.

Alternatively, the cells may be cultured at 37° C. in the presence of 5% $CO_2$ on feeder cells (e.g., mitomycin C-treated STO cells or SNL cells) in the DMEM medium supplemented with 10% FBS (this medium may further contain LIF, penicillin/streptomycin, puromycin, L-glutamine, non-essential amino acids, β-mercaptoethanol and/or the like, as appropriate) for about 25 to about 30 days or longer, to allow ES-like colonies to appear. Preferred examples of the culture method include a method wherein the somatic cells themselves to be reprogrammed are used instead of the feeder cells (Takahashi K, et al. (2009), PLoS One. 4:e8067 or WO2010/137746), and a method wherein an extracellular matrix (e.g., Laminin-5 (WO2009/123349) or Matrigel (BD)) is used instead.

Other examples of the culture method include a method wherein culture is carried out using a serum-free medium (Sun N, et al. (2009), Proc Natl Acad Sci USA. 106:15720-15725). Further, in order to enhance the establishment efficiency, iPS cells may be established under low oxygen conditions (at an oxygen concentration of not less than 0.1% and not more than 15%) (Yoshida Y, et al. (2009), Cell Stem Cell. 5:237-241 or WO2010/013845).

During the culture, the medium is replaced with a fresh medium once every day from Day 2 of the culture. The number of the somatic cells used for nuclear reprogramming is not restricted, and usually within the range of about $5 \times 10^3$ to about $5 \times 10^6$ cells per 100-$cm^2$ area on the culture dish.

iPS cells may be selected based on the shape of each formed colony. In cases where a drug resistance gene was introduced as a marker gene to be expressed in conjunction with a gene that is expressed when a somatic cell was reprogrammed (e.g., Oct3/4 or Nanog), established iPS cells can be selected by culturing the cells in a medium containing the corresponding drug (selection medium). Further, iPS cells can be selected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present description means any animal cells (preferably cells of mammals including human) excluding germ-line cells and totipotent cells such as eggs, oocytes and ES cells. Examples of the somatic cells include, but are not limited to, any of fetal somatic cells, neonatal somatic cells, and mature, healthy and diseased somatic cells, as well as any of primary cultured cells, subcultured cells and established cell lines. Specific examples of the somatic cells include (1) tissue stem cells (somatic stem cells) such as neural stem cells, hematopoietic stem cells, mesenchymal stem cells and dental pulp stem cells; (2) tissue progenitor cells; and (3) differentiated cells such as lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells and adipocytes.

In cases where iPS cells are used as a material for cells to be transplanted, somatic cells whose HLA genotype is the same or substantially the same as that of the individual to which the cells are to be transplanted are preferably used in view of prevention of the rejection reaction. The term "substantially the same" herein means that the HLA genotype is matching to an extent at which the immune reaction against the transplanted cells can be suppressed with an immunosuppressive agent. For example, the somatic cells have matched HLA types at the 3 loci HLA-A, HLA-B and HLA-DR, or at the 4 loci further including HLA-C.

(E) ES Cells Derived from Cloned Embryo Obtained by Nuclear Transfer ntES cells are ES cells derived from a cloned embryo prepared by the nuclear transfer technique, and have almost the same properties as those of ES cells derived from fertilized eggs (T. Wakayama et al. (2001), Science, 292: 740-743; S. Wakayama et al. (2005), Biol. Reprod., 72:932-936; J. Byrne et al. (2007), Nature, 450:497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16:642-646) and the ES cell preparation technique (described above) is employed (Sayaka Wakayama et al. (2008), Experimental Medicine 26(5) (extra edition), pp.

47-52). In nuclear transfer, reprogramming can be achieved by injecting the nucleus of a somatic cell into a mammalian enucleated unfertilized egg and culturing the resultant for several hours.

(F) Multilineage-differentiating Stress Enduring Cells (Muse Cells)

Muse cells are pluripotent stem cells produced by the method described in WO2011/007900. More specifically, Muse cells are cells having pluripotency obtained by subjecting fibroblasts or bone marrow stromal cells to trypsin treatment for a long period, preferably to trypsin treatment for 8 hours or 16 hours, followed by suspension culture of the treated cells. Muse cells are positive for SSEA-3 and CD105.

<Method for Preparing Cell Population Comprising Dopaminergic Neuron Progenitor Cells from Pluripotent Stem Cells>

The method of differentiation induction of pluripotent cells into a cell population comprising dopaminergic neuron progenitor cells is not restricted, and examples of the method include the followings.

Pluripotent stem cells are separated by an arbitrary method and subjected to suspension culture, or adherent culture using a coated culture dish. In the method of separation, the cells may be mechanically separated, or may be separated using an EDTA solution (e.g., 0.5 mM EDTA solution or Versene (Invitrogen)), separation solution having protease activity and collagenase activity (e.g., CTK (collagenase-trypsin-KSR) solution (Suemori H, et al., Biochem Biophys Res Commun. 345: 926-32, 2006), Accutase™ or Accumax™), or separation solution having only collagenase activity. In the suspension culture, a culture dish having a surface which has not been subjected to an artificial treatment for the purpose of enhancing cell adhesiveness such as coating treatment with an extracellular matrix or the like, a culture dish having a surface which has been artificially treated such that adhesion is suppressed (for example, coated with polyhydroxyethylmethacrylate (poly-HEMA)), or a culture dish having a surface treated with Lipidure (NOF Corporation), may be used. In the adherent culture, the culture dish may be one coated with Matrigel (BD), type I collagen, type IV collagen, gelatin, laminin, heparan sulfate proteoglycan or entactin, or a combinations thereof.

The adherent culture may be carried out by co-culturing with feeder cells. Examples of the feeder cells used in the co-culture include PA6 cells (Kawasaki H, et al., Neuron. 2000, 28: 31-40).

A medium to be used for culturing animal cells may be prepared as a basal medium. Examples of the basal medium include GMEM (Glasgow Minimum Essential Medium), IMDM (Iscove's Modified Dulbecco's Medium), Medium 199, Eagle's Minimum Essential Medium (EMEM), aMEM, Dulbecco's modified Eagle's Medium (DMEM), Ham's F12 medium, RPMI 1640 medium and Fischer's medium, and mixtures of these media. The medium is preferably GMEM. The medium may contain serum, but the medium is preferably serum-free to eliminate heterologous components. In such cases, the medium may contain, as required, one or more serum replacements such as albumin, transferrin, fatty acid, insulin, collagen precursor, trace element, Knockout Serum Replacement (KSR) (serum replacement for FBS in ES cell culture) and/or ITS supplement.

The medium may further contain, for promoting survival, growth and differentiation induction of the cells, one or more substances such as 2-mercaptoethanol, thioglycerol, B27 supplement, N2 supplement, lipid, amino acid, L-glutamine, Glutamax (Invitrogen), non-essential amino acid, vitamin, cytokine, hedgehog family, BMP inhibitor, TGFβ family inhibitor, Rho kinase inhibitor, Wnt signaling inhibitor, antibiotic, antioxidant, pyruvic acid, retinoic acid, ascorbic acid, buffer and/or inorganic salt, although the substances are not restricted. Examples of the cytokine include neurotrophic factors and fibroblast growth factors (FGFs), and preferred examples of the cytokine include GDNF, BDNF, FGF-2, FGF-8 and FGF-20. Examples of the hedgehog family include sonic hedgehog (SHH). Examples of the BMP inhibitor include protein-based inhibitors such as Chordin, Noggin and Follistatin; Dorsomorphin (6-[4-(2-piperidin-1-yl-ethoxy)phenyl]-3-pyridin-4-yl-pyrazolo[1,5-a]pyrimidine) and its derivatives (P. B. Yu et al. (2007), Circulation, 116:II_60; P. B. Yu et al. (2008), Nat. Chem. Biol., 4:33-41; J. Hao et al. (2008), PLoS ONE, 3(8):e2904); and LDN-193189 (4-(6-(4-(piperazin-1-yl)phenyl)pyrazolo[1,5-a]pyrimidin-3-yl)quinoline). Dorsomorphin and LDN-193189 are commercially available, and can be obtained from Sigma-Aldrich and Stemgent, respectively. Examples of the TGFβ family inhibitor include Lefty-1 (e.g., NCBI Accession Nos. NM_010094 (mouse) and NM_020997 (human)); SB431542 and SB202190 (these are described in R. K. Lindemann et al., Mol. Cancer, 2003, 2:20); SB505124 (GlaxoSmithKline); NPC30345, SD093, SD908 and SD208 (Scios); LY2109761, LY364947 and LY580276 (Lilly Research Laboratories); A-83-01 (WO 2009146408); and derivatives thereof. Examples of the Rho kinase inhibitor include Fasudil (1-(5-Isoquinolinesulfonyl)homopiperazine Hydrochloride), Y-27632 ((R)-(+)-trans-N-(4-pyridyl)-4-(1-aminoethyl)-cyclohexanecarboxamide.2HCl.H$_2$O), H-1152 (e.g., Sasaki, et al., Pharmacol. Ther. 2002, 93:225-232) and Wf-536 (e.g., Nakajima, et al., Cancer Chemother Pharmacol. 2003, 52(4): 319-324). Examples of the Wnt signaling inhibitor include XAV939 (Shih-Min A. Huang, et al, Nature 461, 614-620, 2009), Dickkopf1 (Dkk1), insulin-like growth factor-binding protein (IGFBP) (WO2009/131166) and siRNAs against β-catenin.

For differentiation induction into a cell population comprising dopaminergic neuron progenitor cells, the medium preferably comprises a BMP inhibitor and TFG β inhibitor.

More preferred examples of the medium include GMEM supplemented with a BMP inhibitor, TGFβ family inhibitor, Rho kinase inhibitor, KSR, pyruvic acid, non-essential amino acid and 2-mercaptoethanol. In cases where additional agents are added, the agents to be added may be different among the stages of culture. More preferably, the cells are cultured for not less than 4 days in the above-described medium, and then cultured in GMEM supplemented with KSR, pyruvic acid, non-essential amino acid and 2-mercaptoethanol with further addition, as required, of FGF-2, FGF-8 and FGF-20.

The culture temperature is not restricted, and preferably about 30 to 40° C., more preferably about 37° C. The culture is carried out under an atmosphere of CO$_2$-containing air, wherein the CO$_2$ concentration is preferably about 2 to 5%. The culture is continued for a period necessary for expression of corin and/or Lmx1a, and, for example, the culture period is not less than 4 days.

The thus produced cell population comprising dopaminergic neuron progenitor cells need not to be a cell population comprising only the single type of cells, and may be a cell population also comprising another/other type(s) of cells.

<Method of Extraction or Detection of Dopaminergic Neuron Progenitor Cells>

Each of the reagent(s) to be used for extracting or detecting dopaminergic neuron progenitor cells from the cell population comprising dopaminergic neuron progenitor cells is not restricted as long as it has specific affinity to CD15 (SSEA-1), CD24, CD46, CD47, CD49b, CD57, CD58, CD59, CD81, CD90, CD98, CD147, CD184, Disalogangliosid GD2, SSEA-4, CD49f, SERINC4, CCR9, PHEX, TMPRSS11E, HTR1E, SLC25A2, Ctxn3, Ccl7, Chrnb4, Chrna3, Kcnv2, Grm2, Syt2, Lim2, Mboat1, St3gal6, Slc39a12, Tacr1, Lrtm1, Dscam, CD201, corin and/or Lmx1a. Antibodies, aptamers, peptides, compounds, and the like which specifically recognize the markers may be used. The reagent is preferably an antibody or its fragment In the present invention, the antibodies may be either a polyclonal or monoclonal antibody. These antibodies can be prepared using a technique well known to those skilled in the art (Current protocols in Molecular Biology edit. Ausubel et al. (1987) Publish. John Wiley and Sons. Sections 11.12-11.13). More specifically, in cases where each antibody is a polyclonal antibody, the polyclonal antibody can be obtained by immunizing a non-human mammal such as a rabbit with a protein such as CD15 (SSEA-1), CD24, CD46, CD47, CD49b, CD57, CD58, CD59, CD81, CD90, CD98, CD147, CD184, Disalogangliosid GD2, SSEA-4, CD49f, SERINC4, CCR9, PHEX, TMPRSS11E, HTR1E, SLC25A2, Ctxn3, Ccl7, Chrnb4, Chrna3, Kcnv2, Grm2, Syt2, Lim2, Mboat1, St3gal6, Slc39a12, Tacr1, Lrtm1, Dscam, CD201, corin or Lmx1a, expressed in E. coli, a mammalian cell line or the like and then purified; an oligopeptide having a partial amino acid sequence of such a protein (preferably the fragments corresponding to extracellular domain(s) of the protein); or a glycolipid; and isolating the polyclonal antibody from the serum of the immunized animal according to a conventional method. In cases where an oligopeptide or glycolipid is used for the immunization, it is preferably cross-linked to an appropriate carrier protein to prepare an immunogen. The carrier protein in such cases is not restricted, and keyhole limpet hemocyanin (KLH), bovine serum albumin (BSA) or the like is often used. In this invention, the protein fragment consisting of a part of sequence of SEQ ID NO: 1 or 2 is exemplified as the fragments corresponding to extracellular domain of mouse and human Lrtm1.

In cases where the antibody is a monoclonal antibody, the monoclonal antibody can be obtained from among hybridoma cells prepared by cell fusion of spleen cells obtained from the above-described immunized non-human mammal with myeloma cells (Current protocols in Molecular Biology edit. Ausubel et al. (1987) Publish. John Wiley and Sons. Sections 11.4-11.11). Examples of the fragment of the antibody include a part of the antibody (e.g., Fab fragment) and a synthetic antibody fragment (e.g., single-stranded Fv fragment "ScFv"). Antibody fragments such as the Fab and F(ab)$_2$ fragments can also be prepared by well known methods such as genetic engineering techniques. Examples of the antibody against corin include the antibody described in WO2006/009241. Examples of the antibody against Lmx1a include the antibody described in WO2005/052190.

Each of the reagents such as antibodies having affinities, which are used for the purpose of recognition or separation of cells expressing CD15 (SSEA-1), CD24, CD46, CD47, CD49b, CD57, CD58, CD59, CD81, CD90, CD98, CD147, CD184, Disalogangliosid GD2, SSEA-4, CD49f, SERINC4, CCR9, PHEX, TMPRSS11E, HTR1E, SLC25A2, Ctxn3, Ccl7, Chrnb4, Chrna3, Kcnv2, Grm2, Syt2, Lim2, Mboat1, St3gal6, Slc39a12, Tacr1, Lrtm1, Dscam, CD201, corin and/or Lmx1a, may be bound or conjugated, for example, to a detectable substance such as a fluorescent label, radioactive label, chemiluminescent label, enzyme, biotin or streptavidin, or to a substance that allows isolation/extraction of the cells, such as protein A, protein G, beads or magnetic beads.

The reagent having affinity may also be indirectly labeled. The labeling may be carried out by various methods known to those skilled in the art, and examples thereof include a method wherein a preliminarily labeled antibody (secondary antibody) that specifically binds to the antibody is used.

Examples of the method for detecting dopaminergic neuron progenitor cells include, but are not limited to, use of a flow cytometer, protein chip or the like.

Examples of the method for extracting dopaminergic neuron progenitor cells include, but are not limited to, a method by conjugating particles to the reagent having affinity, method by sorting cells using magnetic beads by the magnetism (e.g., MACS), method using a fluorescent label to use a cell sorter, and method using a carrier (e.g., cell-concentrating column) to which an antibody or the like is immobilized.

<Application to Regenerative Medicine>

The dopaminergic neuron progenitor cells obtained by the present invention can be effectively used in the field of regenerative medicine for supplying dopaminergic cells which have been lost. Examples of diseases to which the above cells can be applied include Parkinson's disease.

In order to suppress tumorigenesis after transplantation, it is preferred to administer cells that do not express a pluripotency marker(s). Examples of the pluripotency marker(s) herein include Nanog and Oct3/4.

EXAMPLES

The present invention will now be described more specifically by way of Examples below, but, needless to say, the present invention is not restricted to thereto.

Example 1

Human ES cells (KhES-1) were obtained from Institute for Frontier Medical Sciences, Kyoto University (Suemori H, et al. Biochem Biophys Res Commun. 345: 926-32, 2006). Human iPS cells (253G4) were obtained from Center for iPS Cell Research and Application, Kyoto University (Nakagawa M, et al. Nat. Biotechnol. 26:101-6, 2008).

The human ES cells and human iPS cells were induced to differentiate into neural cells by the SDIA (stromal cell-derived inducing activity) method described in Kawasaki H, et al., Neuron. 2000, 28:31-40 which was slightly modified. Briefly, the human ES cells or iPS cells were suspended in CTK (collagenase-trypsin-KSR) solution to form cell clumps (each comprising 10 to 20 cells), which were then plated on PA6 feeders in a 10-cm dish at a ratio of 1:2. The cells were cultured in GMEM (GIBCO) supplemented with 10 µM Y-27632 (ROCK inhibitor, WAKO), 2 µM dorsomorphin (BMP inhibitor, Sigma), 10 µM S13431542 (TGFβ/Activin/Nodal inhibitor, Sigma), 8% KSR, 1 mM pyruvate (Sigma), 0.1 mM MEM non essential amino acid (NEAA, Invitrogen) and 0.1 mM 2-Mercaptoethanol (2-ME, WAKO) for 4 days. The medium was then replaced with GMEM supplemented with 8% KSR, 1 mM pyruvate, 0.1 mM NEAA and 0.1 mM 2-ME, and the culture was continued for 10 to 17 days.

The thus produced cell population comprising dopaminergic neuron progenitor cells were stained using antibodies against human cell surface markers contained in Lyoplate (BD) and an anti-corin antibody (Ono Y, et al., Development 2007, 134:3213-3225), and analyzed by flow cytometry. As a result, the genes and glycolipids described in Table 2 were identified as cell surface markers expressed on corin-positive cells. Further, the gene described in Table 3 was identified as a cell surface marker which is not expressed on corin-positive cells.

TABLE 2

| Marker | NCBI Accession number | |
| --- | --- | --- |
| | Mouse | Homo sapiens |
| CD15 (SSEA-1) | NM_010242 | NM_002033 |
| CD24 | NM_009846 | NM_013230 |
| CD46 | NM_010778 | NM_002389 |
| | | NM_153826 |
| | | NM_172350 |
| | | NM_172351 |
| | | NM_172352 |
| | | NM_172353 |
| | | NM_172359 |
| | | NM_172361 |
| CD47 | NM_010581 | NM_001777 |
| | | NM_198793 |
| CD49b | NM_008396 | NM_002203 |
| CD57 | NM_029792 | NM_018644 |
| | | NM_054025 |
| CD58 | — | NM_001779 |
| | | NM_001144822 |
| CD59 | NM_001111060 | NM_203330 |
| | NM_007652 | NM_000611 |
| | | NM_203329 |
| | | NM_203331 |
| | | NM_001127223 |
| | | NM_001127225 |
| | | NM_001127226 |
| | | NM_001127227 |
| CD81 | NM_133655 | NM_004356 |
| CD90 | NM_009382 | NM_006288 |
| CD98 | NM_001161413 | NM_001012662 |
| (SLC3A2, SLC7A5) | NM_008577 | NM_002394 |
| | NM_011404 | NM_001012664 |
| | | NM_001013251 |
| | | NM_003486 |
| CD147 | NM_001077184 | NM_001728 |
| | NM_009768 | NM_198589 |
| | | NM_198591 |
| CD184 | NM_009911 | NM_001008540 |
| | | NM_003467 |
| Disalogangliosid GD2 | — | — |
| SSEA-4 | — | — |
| CD49f | NM_008397 | NM_000210 |
| | | NM_001079818 |

TABLE 3

| Marker | NCBI Accession number | |
| --- | --- | --- |
| | Mouse | Homo sapiens |
| CD201 | NM_011171 | NM_006404 |

Example 2

Human ES cells (KhES-1) were obtained from Institute for Frontier Medical Sciences, Kyoto University. Human iPS cells (253G4) were obtained from Center for iPS Cell Research and Application, Kyoto University.

The human ES cells and human iPS cells were induced to differentiate into neural cells by the above-described SDIA method and the SFEBq (serum-free embryoid body quick) method described in Eiraku M, et al., Cell Stem Cell. 2008, 3:519-532 which were slightly modified. In the modified SFEBq method, the human ES cells or the human iPS cells were treated with Accumax (Innovate cell technologies) to be suspended into single cells, and then plated on a 96-well plate (Lipidure-coat U96w, Nunc) at 9,000 cells/150 µL/well. The cells were cultured in GMEM supplemented with 10 Y-27632, 0.1 µM LDN193186 (BMP inhibitor, STEMGENT), 0.5 µM A-83-01 (TGFβ/Activin/Nodal inhibitor, WAKO), 8% KSR, 1 mM pyruvate, 0.1 mM NEAA and 0.1 mM 2-ME for 5 days. The medium was then replaced with GMEM supplemented with 8% KSR, 1 mM pyruvate, 0.1 mM NEAA and 0.1 mM 2-ME, and the culture was continued for 5 to 9 days.

From the cell population comprising dopaminergic neuron progenitor cells produced by the modified SDIA method or modified SFEBq method, corin-positive cells and corin-negative cells were sorted with a flow cytometer. By the microarray method, genes specifically showing higher expression in corin-positive cells relative to corin-negative cells were identified. Among the genes which specifically showed high expression, cell surface markers were as shown in Table 4.

TABLE 4

| Marker | NCBI Accession number | |
| --- | --- | --- |
| | mouse | Homo sapiens |
| SERINC4 | NM_001025371 | NM_001033517 |
| CCR9 | NM_001166625 | NM_006641 |
| | NM_009913 | NM_031200 |
| PHEX | NM_011077 | NM_000444 |
| TMPRSS11E | NM_172880 | NM_014058 |
| HTR1E | — | NM_000865 |
| SLC25A2 | NM_001159275 | NM_031947 |

Example 3

Mouse ES cells in which the GFP gene was knocked-in into the Lmx1a locus and GFP expression is regulated by the endogenous Lmx1a promoter were induced to differentiate into neural cells by the SFEB method. Briefly, the ES cells were suspended in GMEM supplemented with 2 mM L-Gln, 0.1 mM NEAA, 1 mM Sodium pyruvate, 0.1 mM 2-ME and 5% KSR, and subjected to suspension culture using a 96-well plate at a density of 3,000 cells/150 µl/well. On Day 3 of the suspension culture, 100 ng/ml FGF8 was added to the medium. On the next day, 100 ng/ml SHH was added to the medium. On Day 7 of the suspension culture, the medium was replaced with GMEM supplemented with 100 ng/ml SHH, 20 ng/ml BDNF, 200 nM Ascorbic acid, 2 mM L-Gln, 0.1 mM NEAA, 1 mM Sodium pyruvate and 0.1 mM 2-ME. On Day 11 of the suspension culture, the cells were collected, and 4 fractions, that is, (1) GFP (Lmx1a)-positive and corin-positive; (2) GFP (Lmx1a)-positive and corin-negative; (3) GFP (Lmx1a)-negative and corin-positive; and (4) GFP (Lmx1a)-negative and corin-negative; were separated using a flow cytometer. By the microarray method, genes which were more strongly expressed in the fractions (1), (2) and (3) than in the fraction (4) were identified. Among the thus identified genes specifically expressed in the corin- and/or Lmx1a-positive cells, cell surface markers were as shown in Table 5.

TABLE 5

| Marker | NCBI Accession number | |
|---|---|---|
| | mouse | homo sapiens |
| Ctxn3 | NM_001134697 | NM_001048252 |
| | | NM_001127385 |
| Ccl7 | NM_013654 | NM_006273 |
| Chmb4 | NM_148944 | NM_000750 |
| Chrna3 | NM_145129 | NM_000743 |
| | | NM_001166694 |
| Kcnv2 | NM_183179 | NM_133497 |
| Grm2 | NM_001160353 | NM_000839 |
| | | NM_001130063 |
| Syt2 | NM_009307 | NM_001136504 |
| | | NM_177402 |
| Lim2 | NM_177693 | NM_001161748 |
| | | NM_030657 |
| Mboat1 | NM_153546 | NM_001080480 |
| St3gal6 | NM_018784 | NM_006100 |
| Slc39a12 | NM_001012305 | NM_001145195 |
| Tacr1 | NM_009313 | NM_001058 |
| | | NM_015727 |
| Lrtm1 | NM_176920 | NM_020678 |
| Dscam | NM_031174 | NM_001389 |

Example 4

Mouse iPS cells (440A-3) were obtained from RIKEN BRC (Okita K et al. Science 322: 949-953 (2008)).

The mouse iPS cells were induced to differentiate into neural cells by the following SFEBq method;
Day 0: The mouse iPS cells were dissociated into single cells, and then plated on a 96-well plate (Lipidure-coat U96w, Nunc) at 6,000 cells/150 µL/well. The cells were cultured in mSFEB Medium (GMEM supplemented with 2 mM L-Glutamine, 1 mM Sodium pyruvate, 0.1 mM NEAA and 1 mM 2-ME) supplemented with 5% KSR.
Day 1: Half medium was replaced with mSFEB Medium supplemented with 5% KSR, 200 ng/µl rhFGF8b (Peprotech) and 200 ng/µl rmSHH(R&D).
Day 3: Half medium was replaced with SFEB Medium supplemented with 5% KSR, 100 ng/µl rhFGF8b and 100 ng/µl rmSHH.
Day 5: Half medium was replaced with SFEB Medium supplemented with 5% KSR, 100 ng/µl rhFGF8b and 100 ng/µl rmSHH.
Day 7: Half medium was replaced with SFEB Medium supplemented with N2, 200 nM Ascorbic acid and 20 ng/ml rhBDNF.
Day 9: The cells were dissociated into the single cells with Accutase. FACS buffer (PBS supplemented with 20 mM Glucose (Wako) and 2% FBS (Cell culture bioscience)) was added to the cell solution, and then immunostained with monoclonal anti-mLrtm1 antibodies at 4 degree C. for 20 min. Stained cells and unstained cells were sorted with FACSAriaII (BD Biosciences), and then plated on 8 well chamber (OFL (Poly-L-ornithine, Fibronectin and Laminin)-coat) at 50,000 cells/well. The cells were cultured in mAdhesion Medium (DMEM/F12 supplemented with 2 mM L-Glutamine, N2, B27, 200 nM Ascorbic acid, 20 ng/ml rhBDNF, 10 ng/ml rhGDNF, 1% KSR, Penicillin Streptomycin) supplemented with 30 µM Y-27632. The monoclonal anti-mLrtm1 antibodies were obtained from the culture supernatant of myeloma fusion cells. The fusion cells were produced with well-known method. Briefly, rat were immunized with isolated protein consisting of the extracellular region encoding sequence in mouse Lrtm1 gene, and lymphocytes were removed therefrom and fused with myeloma cells. The anti-mLrtm1 antibody is checked by recognition of the transfectant cells overexpressing mouse Lrtm1 and mouse embryonic midbrain.
Day 11: All medium was replaced with mAdhesion Medium.
Day 14: All medium was replaced with mAdhesion Medium.

Figure 2:
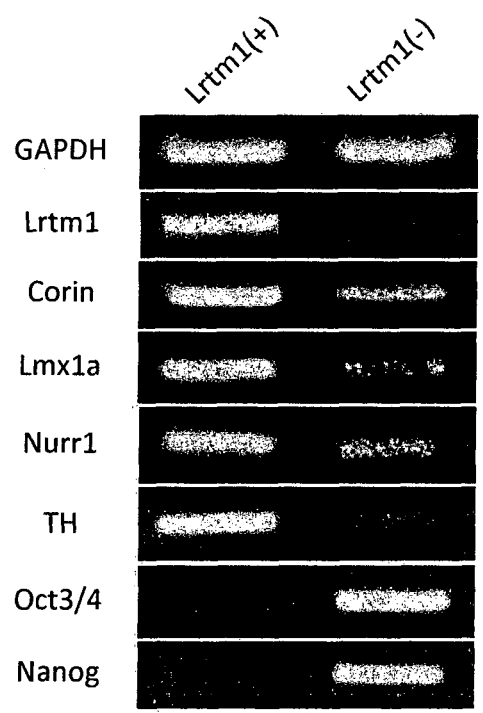
FIG. 2A shows PCR analysis for mouse Lrtm1 positive and negative cells just after sorting (photograph).
FIG. 2B shows growth chart of the cells after sorting.
Figure 2:
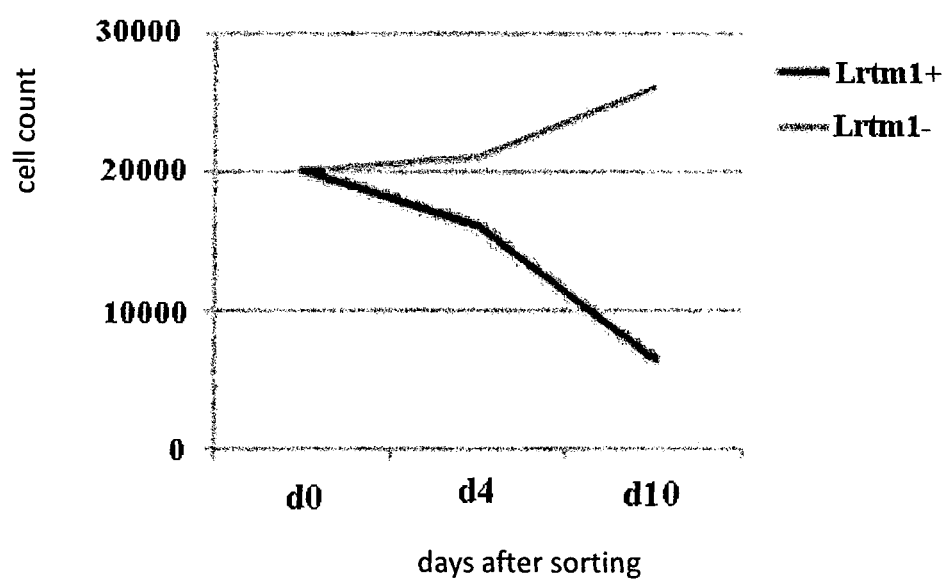

At 0 and 7 days after sorting, the cells were analyzed with PCR and immunostaining. The result is shown in FIGS. 1 and 2. The content rate of each neural marker positive cells is shown in Table 6 and 7. Just after sorting, Lmx1a and Corin positive cells were frequently confirmed in Lrtm1 positive cells. Similarly, at 7 days after sorting, dopaminergic neuron marker positive cells were frequently confirmed in Lrtm1 positive cells. Furthermore, the Lrtm1 positive cells did not proliferate after sorting. These results show that Lrtm1 can be substituted for Lmx1a and Corin and one of the potent marker for postmitotic dopaminergic neuron progenitor cells.

TABLE 6

Day 0 after sorting

| | Sorted cells by Lrtm1positive gate | Sorted sells by Lrtm1negative gate |
|---|---|---|
| Rate of Lmx1a positive cells to DAPI positive nuclei | 56.8% | 9.9% |
| Rate of Corin positive cells to DAPI positive nuclei | 54.0% | 5.3% |
| Rate of Corin and Lmx1a positive cells to DAPI positive nuclei | 42.7% | 2.6% |

TABLE 7

Day 7 after sorting

| | Sorted cells by Lrtm1positive gate | Sorted sells by Lrtm1negative gate |
|---|---|---|
| Rate of TH positive cells to DAPI positive nuclei | 32.3% | 7.4% |
| Rate of TH positive cells to Tuj1 positive cells | 37.1% | 15.5% |
| Rate of Nurr1 positive cells to TH positive cells | 57.1% | 7.9% |
| Rate of DAT positive cells to DAPI positive nuclei | 30.7% | 2.2% |

Example 5

Human ES cells (Kh-ES 1) were induced to differentiate into neural cells by the following SFEBq method;
Day 0: The human ES cells were treated with Accumax (Innovate cell technologies) to be suspended into single cells, and then plated on a 96-well plate (Lipidure-coat U96w, Nunc) at 6,000 cells/150 µL/well. The cells were cultured in hSFEB Medium (GMEM supplemented with 1 mM Sodium pyruvate, 0.1 mM NEAA and 1 mM 2-ME) supplemented with 8% KSR, 0.1 µM LDN193186, 0.5 µM A-83-01 and 30 µM Y-27632,
Day 1: Half medium was replaced with hSFEB Medium supplemented with 8% KSR, 0.1 µM LDN193186, 0.5 µM A-83-01, 30 µM Y-27632, 100 ng/µl rhFGF8b (Peprotech), 100 ng/µl rmSHH(R&D) and 4 µM Purmorphamine (Wako).
Day 3: Half medium was replaced with hSFEB Medium supplemented with 8% KSR, 0.1 µM LDN193186, 0.5 µM A-83-01, 30 μM Y-27632, 100 ng/μl rhFGF8b, 100 ng/μl rmSHH, 2 μM Purmorphamine and 6 μM CHIR99021.

Day 5: Half medium was replaced with hSFEB Medium supplemented with 8% KSR, 0.1 μM LDN193186, 100 ng/μl rhFGF8b, 100 ng/μl rmSHH, 2 μM Purmorphamine and 3 μM CHIR99021.

Day 7: Half medium was replaced with hSFEB Medium supplemented with 8% KSR and 3 μM CHIR99021.

Day 9: Half medium was replaced with hSFEB Medium supplemented with 8% KSR and 3 μM CHIR99021.

Day 12: The cells were dissociated into the single cells with Accutase. FACS buffer (PBS supplemented with 20 mM Glucose (Wako) and 2%0 FBS (Cell culture bioscience)) was added to the cell solution, and then immunostained with monoclonal anti-hLrtm1 antibodies at 4 degree C. for 20 min. Stained cells and unstained cells were sorted with FACSAriaII (BD Biosciences), and then plated on 8 well chamber (OL (Poly-L-ornithine and Laminin)-coat) at 50,000 cells/well. The cells were cultured in hAdhesion Medium (Neurobasal supplemented with 2 mM L-Glutamine, B27, 200 nM Ascorbic acid, 20 ng/ml rhBDNF, 10 ng/ml rhGDNF, Penicillin Streptomycin) supplemented with 30 μM Y-27632. The monoclonal anti-hLRTM 1 antibodies were obtained from the culture supernatant of myeloma fusion cells. The fusion cells were produced with well-known method. Briefly, rat were immunized with isolated protein consisting of the extracellular region encoding sequence in human LRTM1 gene, and lymphocytes were removed therefrom and fused with myeloma cells. The anti-hLRTM 1 antibody is checked by recognition of the transfectant cells overexpressing human LRTM1.

Day 14: All medium was replaced with hAdhesion Medium.
Day 17: All medium was replaced with hAdhesion Medium.

Figure 3:
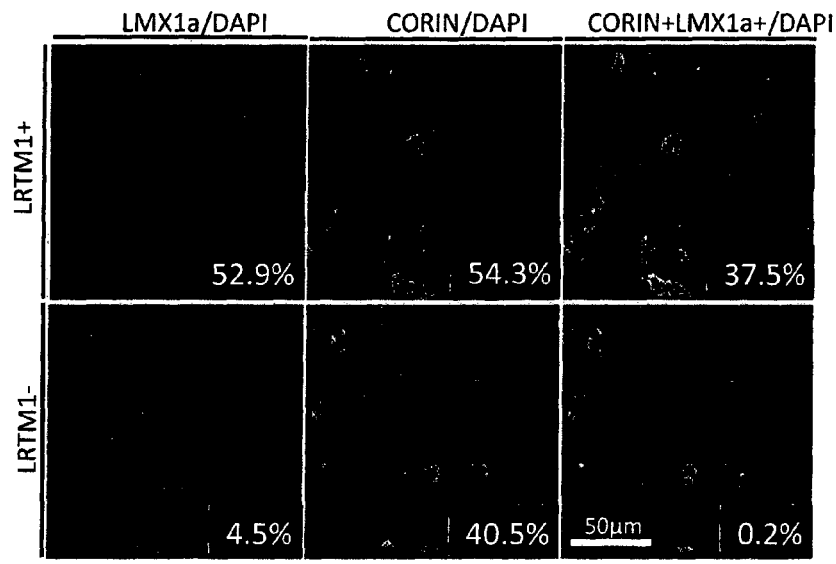
FIG. 3 shows fluorescent image for immunostaining (photograph).
Figure 3:
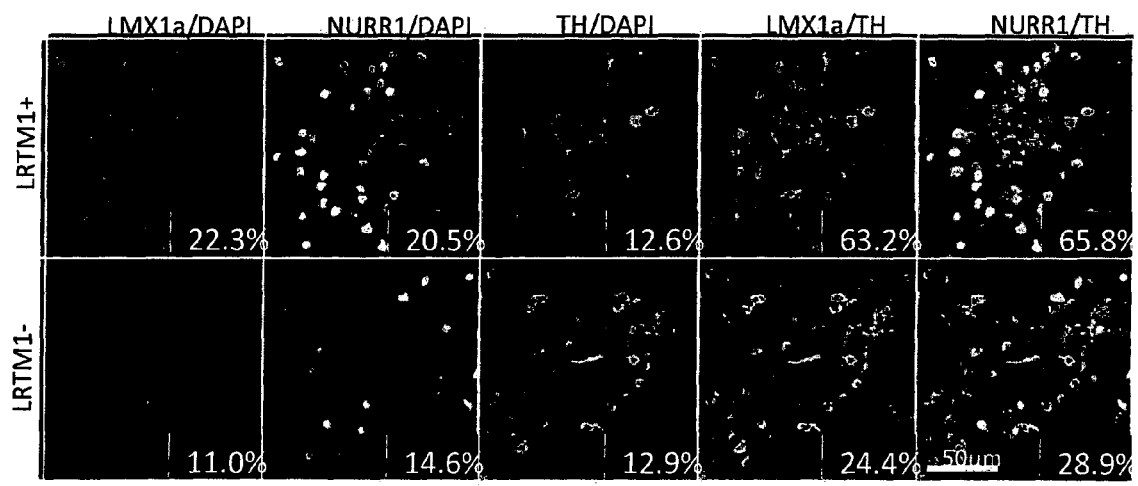

At 0 and 7 days after sorting, the cells were analyzed with immunostaining. The result is shown in FIG. 3. The content rate of each neural marker positive cells is shown in Table 8 and 9. At 0 and 7 days after sorting, LMX1a positive cells were frequently confirmed in Lrtm1 positive cells. These results show that LRTM1 can be substituted for LMX1a. At 7 days after sorting, NURR1 positive cells in LRTM1 positive cells were contained in TH positive cells at a relatively high percentage. Lrtm1 is one of the cell membrane protein. Therefore, alive dopaminergic neuron progenitor cells can be extracted by using the LRTM1 as a marker.

TABLE 8

Day 0 after sorting

|  | Sorted cells by LRTM1positive gate | Sorted sells by LRTM1negative gate |
|---|---|---|
| Rate of Lmx1a positive cells to DAPI positive nuclei | 52.9% | 4.5% |
| Rate of Corin positive cells to DAPI positive nuclei | 54.3% | 40.5% |
| Rate of Corin and Lmx1a positive cells to DAPI positive nuclei | 37.5% | 0.2% |

TABLE 9

Day 7 after sorting

|  | Sorted cells by LRTM1positive gate | Sorted sells by LRTM1negative gate |
|---|---|---|
| Rate of Lmx1a positive cells to DAPI positive nuclei | 22.3% | 11.0% |
| Rate of Nurr1 positive cells to DAPI positive nuclei | 20.5% | 14.6% |
| Rate of Tyrosine Hydroxylase (TH) positive cells to DAPI positive nuclei | 12.6% | 12.9% |
| Rate of Lmx1a positive cells to TH positive cells | 63.2% | 24.4% |
| Rate of Nurr1 positive cells to TH positive cells | 65.8% | 28.9% |

What is claimed is:

1. A method for producing dopaminergic neuron progenitor cells, said method comprising:
   (i) inducing a cell population comprising dopaminergic neuron progenitor cells from pluripotent stem cells; and
   (ii) extracting from the cell population cells expressing Lrtm1, wherein cells expressing Lrtm1 are extracted from the cell population by contacting the cell population with one or more reagents having specific affinity to Lrtm1 and extracting cells that bind to the one or more reagents having specific affinity to Lrtm1, and wherein the extracted cells comprise dopaminergic neuron progenitor cells.

2. The method according to claim 1, further comprising extracting corin and/or Lmx1a positive cells from the cells extracted in step (ii), wherein cells expressing corin and/or Lmx1a are extracted from the cell population by contacting the cell population with one or more reagents having specific affinity to corin and/or Lmx1a and extracting cells that bind to the one or more reagents.

3. The method according to claim 1, wherein said dopaminergic neuron progenitor cells are human dopaminergic neuron progenitor cells.

4. The method according to claim 1, wherein said cell population is induced from pluripotent stem cells by culturing the pluripotent stem cells in a medium supplemented with a BMP inhibitor and a TGFβ inhibitor in step (i).

5. The method according to claim 1, wherein cells expressing Lrtm1 are extracted from the cell population by contacting the cell population with one or more antibodies that bind to Lrtm1 and extracting cells that bind to the one or more antibodies.

6. A method for enriching dopaminergic neuron progenitor cells, said method comprising:
   (i) providing a cell population comprising dopaminergic neuron progenitor cells, wherein the cell population is induced from pluripotent stem cells or the cell population is composed of cells of an isolated tissue or tissues; and
   (ii) extracting from the cell population cells expressing Lrtm1, wherein cells expressing Lrtm1 are extracted from the cell population by contacting the cell population with one or more reagents having specific affinity to Lrtm1 and extracting cells that bind to the one or more reagents, and wherein the extracted cells comprise dopaminergic neuron progenitor cells.

7. The method according to claim 6, wherein cells expressing Lrtm1 are extracted from the cell population by contacting the cell population with one or more antibodies that bind to Lrtm1 and extracting cells that bind to the one or more antibodies.

* * * * *